US008163294B2

(12) United States Patent
Horwitz et al.

(10) Patent No.: US 8,163,294 B2
(45) Date of Patent: Apr. 24, 2012

(54) GROWTH REGULATABLE RECOMBINANT BCG COMPOSITIONS

(75) Inventors: Marcus A. Horwitz, Los Angeles, CA (US); Michael V. Tullius, Encino, CA (US)

(73) Assignee: The Regents of the University of California, Oakland, CA (US)

( * ) Notice: Subject to any disclaimer, the term of this patent is extended or adjusted under 35 U.S.C. 154(b) by 518 days.

(21) Appl. No.: 12/296,660

(22) PCT Filed: Apr. 10, 2007

(86) PCT No.: PCT/US2007/066348
§ 371 (c)(1),
(2), (4) Date: Apr. 22, 2009

(87) PCT Pub. No.: WO2007/121193
PCT Pub. Date: Oct. 25, 2007

(65) Prior Publication Data

US 2010/0284963 A1 Nov. 11, 2010

Related U.S. Application Data

(63) Continuation-in-part of application No. 10/595,385, filed as application No. PCT/US2004/034206 on Oct. 15, 2006, now Pat. No. 7,622,107.

(60) Provisional application No. 60/744,552, filed on Apr. 10, 2006, provisional application No. 60/512,565, filed on Oct. 16, 2003.

(51) Int. Cl.
*A61K 39/04* (2006.01)
*A61K 39/02* (2006.01)
*A61K 49/00* (2006.01)

(52) U.S. Cl. .... 424/248.1; 424/9.1; 424/9.2; 424/184.1; 424/192.1; 424/200.1; 424/234.1

(58) Field of Classification Search .................. 424/9.1, 424/9.2, 184.1, 192.1, 200.1, 234.1, 248.1
See application file for complete search history.

(56) References Cited

U.S. PATENT DOCUMENTS

| | | | | |
|---|---|---|---|---|
| 5,504,005 | A | 4/1996 | Bloom et al. | |
| 5,830,475 | A | 11/1998 | Aldovini et al. | |
| 5,854,055 | A | 12/1998 | Bloom et al. | |
| 6,599,510 | B1 | 7/2003 | Horwitz et al. | |
| 6,924,118 | B2 * | 8/2005 | Horwitz et al. | 424/9.1 |
| 2004/0009184 | A1 * | 1/2004 | Horwitz et al. | 424/184.1 |

FOREIGN PATENT DOCUMENTS

| | | |
|---|---|---|
| WO | 2004031356 | 4/2004 |
| WO | 2005037222 | 4/2005 |

OTHER PUBLICATIONS

Horwitz, Marcus, et al., "Recombinant bacillus Calmette-Guerin (BCG) vaccines expressing the *Mycobacterium tuberculosis* 30-kDa major secretory protein induce greater protective immunity against tuberculosis than conventional BCG vaccines in a highly susceptible animal model", Proceedings of the National Academy of Sciences of USA, National Academy of Science, vol. 97, No. 25, Dec. 5, 2000, pp. 13853-13858.

Sambandamurthy, Vasan K., et al., "A pantothenate auxotroph of *Myobacterium tuberculosis* is highly attenuated and protects mice against tuberculosis", Nature Medicine, vol. 8, No. 10, Oct. 2002, pp. 1171-1174.

Smith, D.A., et al., "Characterization of auxotrophic mutants of *Mycobacterium tuberculosis* and their potential as vaccine candidates", Infection and Immunity, vol. 69, No. 2, Feb. 2001, pp. 1142-1150.

Bardarov, Stoyan, et al., "Specialized transduction: an efficient method for generating marked and unmarked targeted gene disruptions in *Mycobacterium tuberculosis*, *M. bovis* BCG and *M. smegmatis*", Microbiology, vol. 148, 2002, pp. 3007-3017.

Howard, Nathan S., et al., "Color selection with a hygromycin-resistance-based *Escherichia coli*-mycobacterial schuttle vector", Gene, vol. 168, 1995, pp. 181-182.

* cited by examiner

*Primary Examiner* — Rodney P. Swartz

(74) *Attorney, Agent, or Firm* — K&L Gates LLP; Louis C. Cullman; Michelle Glasky Bergman

(57) ABSTRACT

Immunogenic compositions comprising growth regulatable recombinant attenuated intracellular pathogens that have been transformed to express recombinant immunogenic antigens of the same or other intracellular pathogens are provided. Exemplary immunogenic compositions include, growth regulatable and growth limited recombinant attenuated intracellular pathogen immunogenic compositions.

17 Claims, 7 Drawing Sheets

GROWTH REGULATABLE RECOMBINANT BCG COMPOSITIONS

CROSS REFERENCE TO RELATED APPLICATIONS

This application claims the benefit under 35 U.S.C. §371 to PCT/2007/66348 filed Apr. 10, 2007, which claims the benefit under 35 U.S.C. §119(e) to U.S. Provisional Patent Application No. 60/774,552 filed Apr. 10, 2006, and is a continuation-in-part of U.S. patent application Ser. No. 10/595,385, now U.S. Pat. No. 7,622,107, which is a national phase application of International Application No. PCT/US04/34206 filed Oct. 15, 2006 and which claims the benefit under 35 U.S.C. §119(e to U.S. Provisional Patent Application 60/512,565 filed Oct. 16, 2003. The entire contents of each of these applications are incorporated by reference herein.

STATEMENT REGARDING FEDERALLY SPONSORED RESEARCH

This invention was made with Government support under Grant Nos. A131338 and A1068413 awarded by the Department of Health and Human Services. The Government has certain rights in this invention.

FIELD OF THE INVENTION

The present invention generally relates to immunogenic compositions derived from recombinant intracellular pathogenic bacteria. Moreover, the immunogenic compositions of the present invention also comprise growth regulatable recombinant attenuated *Mycobacteria* including auxotrophic, prototrophic and metabolically impaired strains. The immunogenic compositions of the present invention are useful in inducing immune responses in hosts.

BACKGROUND OF THE INVENTION

It has long been recognized that parasitic microorganisms possess the ability to infect animals thereby causing disease and often death. Pathogenic agents have been a leading cause of death throughout history and continue to inflict immense suffering. Though the last hundred years have seen dramatic advances in the prevention and treatment of many infectious diseases, complicated host-parasite interactions still limit the universal effectiveness of therapeutic measures. Difficulties in countering the sophisticated invasive mechanisms displayed by many pathogenic organisms are evidenced by the resurgence of various diseases such as tuberculosis, as well as the appearance of numerous drug resistant strains of bacteria and viruses.

Among those pathogenic agents of major epidemiological concern, intracellular bacteria have proven to be particularly intractable in the face of therapeutic or prophylactic measures. Intracellular bacteria, including the genus *Mycobacterium*, complete all or part of their lifecycle within the cells of the infected host organism rather than extracellularly. Around the world, intracellular bacteria are responsible for untold suffering and millions of deaths each year. Tuberculosis is the leading cause of death from a single disease agent worldwide, with 8 million new cases and 2 million deaths annually. In addition, intracellular bacteria are responsible for millions of cases of leprosy. Other debilitating diseases transmitted by intracellular agents include cutaneous and visceral leishmaniasis, American trypanosomiasis (Chagas disease), listeriosis, toxoplasmosis, histoplasmosis, trachoma, psittacosis, Q-fever, legionellosis, anthrax, and tularemia.

Currently it is believed that approximately one-third of the world's population is infected by *Mycobacterium tuberculosis* resulting in millions of cases of pulmonary tuberculosis annually. More specifically, human pulmonary tuberculosis primarily caused by *M. tuberculosis* is a major cause of death in developing countries. *Mycobacterium tuberculosis* is capable of surviving inside macrophages and monocytes, and therefore may produce a chronic intracellular infection. *Mycobacterium tuberculosis* is relatively successful in evading the normal defenses of the host organism by concealing itself within the cells primarily responsible for the detection of foreign elements and subsequent activation of the immune system. Moreover, many of the front-line chemotherapeutic agents used to treat tuberculosis have relatively low activity against intracellular organisms as compared to extracellular forms. These same pathogenic characteristics have heretofore limited the effectiveness of immunotherapeutic agents or immunogenic compositions against tubercular infections.

Recently, tuberculosis resistance to one or more drugs was reported in 36 of the 50 United States. In New York City, one-third of all cases tested was resistant to one or more major drugs. Though non-resistant tuberculosis can be cured with a long course of antibiotics, the outlook regarding drug resistant strains is bleak. Patients infected with strains resistant to two or more major antibiotics have a fatality rate of around 50%. Accordingly, safe and effective immunogenic compositions against multi-drug resistant strains of *M. tuberculosis* are sorely needed.

Initial infections of *M. tuberculosis* almost always occur through the inhalation of aerosolized particles as the pathogen can remain viable for weeks or months in moist or dry sputum. Although the primary site of the infection is in the lungs, the organism can also cause infection of nearly any organ including, but not limited to, the bones, spleen, kidney, meninges and skin. Depending on the virulence of the particular strain and the resistance of the host, the infection and corresponding damage to the tissue may be minor or extensive. In the case of humans, the initial infection is controlled in the majority of individuals exposed to virulent strains of the bacteria. The development of acquired immunity following the initial challenge reduces bacterial proliferation thereby allowing lesions to heal and leaving the subject largely asymptomatic.

When *M. tuberculosis* is not controlled by the infected subject it often results in the extensive degradation of lung tissue. In susceptible individuals, lesions are usually formed in the lung as the tubercle bacilli reproduce within alveolar or pulmonary macrophages. As the organisms multiply, they may spread through the lymphatic system to distal lymph nodes and through the blood stream to the lung apices, bone marrow, kidney and meninges surrounding the brain. Primarily as the result of cell-mediated hypersensitivity responses, characteristic granulomatous lesions or tubercles are produced in proportion to the severity of the infection. These lesions consist of epithelioid cells bordered by monocytes, lymphocytes and fibroblasts. In most instances a lesion or tubercle eventually becomes necrotic and undergoes caseation (conversion of affected tissues into a soft cheesy substance).

While *M. tuberculosis* is a significant pathogen, other species of the genus *Mycobacterium* also cause disease in animals including man and are clearly within the scope of the present invention. For example, *M. bovis* is closely related to *M. tuberculosis* and is responsible for tubercular infections in domestic animals such as cattle, pigs, sheep, horses, dogs and cats. Further, *M. bovis* may infect humans via the intestinal tract, typically from the ingestion of raw milk. The localized intestinal infection eventually spreads to the respiratory tract and is followed shortly by the classic symptoms of tuberculosis. Another important pathogenic species of the genus *Mycobacterium* is *M. leprae* that causes millions of cases of the ancient disease leprosy. Other species of this genus which cause disease in animals and man include *M. kansasii, M. avium* intracellulare, *M. fortuitum, M. marinum, M. chelonei*, and *M. scrofulaceum*. The pathogenic mycobacterial species frequently exhibit a high degree of homology in their respective DNA and corresponding protein sequences and some species, such as *M. tuberculosis* and *M. bovis*, are highly related.

Attempts to eradicate tuberculosis using immunogenic compositions was initiated in 1921 after Calmette and Guérin successfully attenuated a virulent strain of *M. bovis* at the Institut Pasteur in Lille, France. This attenuated *M. bovis* became known as the Bacille Calmette Guérin, or BCG for short. Nearly eighty years later, immunogenic compositions derived from BCG remain the only prophylactic therapy for tuberculosis currently in use. In fact, all BCG immunogenic compositions available today are derived from the original strain of *M. bovis* developed by Calmette and Guérin at the Institut Pasteur.

The World Health Organization considers the BCG immunogenic compositions an essential factor in reducing tuberculosis worldwide, especially in developing nations. In theory, the BCG immunogenic composition confers cell-mediated immunity against an attenuated mycobacterium that is immunologically related to *M. tuberculosis*. The resulting immune response should inhibit primary tuberculosis. Thus, if primary tuberculosis is inhibited, latent infections cannot occur and disease reactivation is avoided.

Current BCG immunogenic compositions are provided as lyphophilized cultures that are re-hydrated with sterile diluent immediately before administration. The BCG immunogenic composition is given at birth, in infancy, or in early childhood in countries that practice BCG vaccination, including developing and developed countries. Adult visitors to endemic regions who may have been exposed to high doses of infectious *Mycobacteria* may receive BCG as a prophylactic providing they are skin test non-reactive. Adverse reactions to the immunogenic composition are rare and are generally limited to skin ulcerations and lymphadenitis near the injection site. However, in spite of these rare adverse reactions, the BCG immunogenic composition has an unparalleled history of safety with over three billion doses having been administered worldwide since 1930.

However, the unparalleled safety of traditional BCG immunogenic compositions is coming under increased scrutiny and has created a paradox for healthcare practitioners. In immunocompromised individuals, BCG can disseminate and cause serious and even fatal disease. The World Health Organization has recommended that the BCG vaccine not be administered to immunocompromised HIV-positive persons. The population segments most susceptible to mycobacterial infections are the immunocompromised and immunosuppressed. Persons suffering from early or late-stage HIV infections are particularly susceptible to infection. Unfortunately, many persons in the early-stage of HIV infection are unaware of their immune status. It is likely that these individuals may voluntarily undergo immunization using a live attenuated immunogenic composition such as BCG without being forewarned of their unique risks. Moreover, other mildly immunocompromised or immunosuppressed individuals may also unwittingly undergo immunization with BCG hoping to avoid mycobacterial disease. Therefore, safer, more efficacious BCG and BCG-like immunogenic compositions are desirable.

Recently, significant attention has been focused on using transformed BCG strains to produce immunogenic compositions that express various cell-associated antigens. For example, C. K. Stover, et al. have reported a Lyme Disease immunogenic composition using a recombinant BCG (rBCG) that expresses the membrane associated lipoprotein OspA of *Borrelia burgdorferi*. Similarly, the same author has also produced a rBCG immunogenic composition expressing a pneumococcal surface protein (PsPA) of *Streptococcus pneumoniae*. (Stover C K, Bansal G P, Langerman S, and Hanson M S. 1994. Protective immunity elicited by rBCG immunogenic compositions. In: Brown F. (ed): Recombinant Vectors in Immunogenic composition Development. Dev Biol Stand. Dasel, Karger, Vol. 82:163-170)

U.S. Pat. No. 5,504,005 (the "'005" patent") and U.S. Pat. No. 5,854,055 (the "'055 patent") both issued to B. R. Bloom et al., disclose theoretical rBCG vectors expressing a wide range of cell-associated fusion proteins from numerous species of microorganisms. The theoretical vectors described in these patents are either directed to cell associated fusion proteins, as opposed to extracellular non-fusion protein antigens, and/or the rBCG is hypothetically expressing fusion proteins from distantly related species.

Furthermore, neither the '005 nor the '055 patent disclose animal model safety testing, immune response development or protective immunity in an animal system that closely emulates human disease. In addition, only theoretical rBCG vectors expressing *M. tuberculosis* fusion proteins are disclosed in the '005 and '055 patents; no actual immunogenic compositions are enabled. Those immunogenic composition models for *M. tuberculosis* that are disclosed are directed to cell-associated heat shock fusion proteins, not extracellular non-fusion proteins.

U.S. Pat. No. 5,830,475 (the "'475 patent") also discloses theoretical mycobacterial immunogenic compositions used to express fusion proteins. The immunogenic compositions disclosed are intended to elicit immune responses in non-human animals for the purpose of producing antibodies thereto and not shown to prevent intracellular pathogen diseases in mammals. Moreover, the '475 patent does not disclose recombinant immunogenic compositions that use protein specific promoters to express extracellular non-fusion proteins.

U.S. Pat. No. 6,471,967, claims immunogenic compositions comprising a recombinant BCG having an extrachromosomal nucleic acid sequence comprising a gene encoding a *M. tuberculosis* 30 kDa major extracellular protein (also known as Antigen 85B), wherein the *M. tuberculosis* 30 kDa major extracellular protein is over-expressed and secreted. Moreover, U.S. Pat. No. 6,924,118 claims additional recombinant BCG that over-express other *M. tuberculosis* major extracellular proteins.

Therefore, there remains a need for intracellular pathogen immunogenic compositions that can be safely administered to immunosuppressed, or partially immunosuppressed, individuals.

SUMMARY OF THE INVENTION

The present invention provides methods for producing recombinant immunogenic compositions for preventing or treating diseases of intracellular pathogens in humans and animals, immunogenic compositions against diseases of intracellular pathogens in humans and animals, and a new approach to producing immunogenic composition against tuberculosis, leprosy, other mycobacterial diseases, and other intracellular pathogens.

The present invention provides recombinant Bacille Calmette Guérin (rBCG) immunogenic compositions that a) are growth-limited and/or growth-regulatable and b) are growth-limited and/or growth-regulatable and secrete a major extracellular protein of an intracellular pathogen, in one non-limiting example, a *Mycobacterium tuberculosis* major extracellular protein. The growth-regulatable compositions of the present invention are auxotrophic or siderophore-dependent.

In one embodiment of the present invention, an immunogenic composition is provided comprising a growth regulatable recombinant Bacille Calmette Guérin (rBCG) expressing at least one *Mycobacteria* major extracellular protein selected from the group consisting of 12 kDa protein, 14 kDa protein, 16 kDa protein, 23.5 kDa protein, 24 kDa protein, 30 kDa protein, 32A kDa protein, 32B kDa protein, 45 kDa protein, 58 kDa protein, 71 kDa protein, 80 kDa protein, and 110 KD protein, and combinations thereof, and wherein the *Mycobacteria* major extracellular proteins are over-expressed and secreted.

In another embodiment of the present invention, at least one of the at least one *Mycobacteria* major extracellular proteins are expressed on one or more extrachromosomal nucleic acid sequences. In another embodiment, more than one of the at least one *Mycobacteria* major extracellular proteins are expressed on one or more extrachromosomal nucleic acid sequences. In another embodiment, each of said at least one *Mycobacteria* major extracellular proteins are expressed from different extrachromosomal nucleic acid sequences.

In another embodiment, at least one of said at least one *Mycobacteria* major extracellular proteins are integrated into the rBCG genome under the control of a strong promoter and over-expressed. In another embodiment, more than one of the at least one *Mycobacteria* major extracellular proteins are integrated into the rBCG genome under the control of a strong promoter and over-expressed.

In another embodiment, the major extracellular proteins are non-fusion proteins. In another embodiment, the major extracellular proteins are fusion proteins under the control of a strong promoter.

In another embodiment of the present invention, the immunogenic composition is a growth regulatable rBCG is selected from the group consisting of auxotrophs and metabolically impaired mutants. In another embodiment, the metabolically impaired mutant is a siderophore mutant. In another embodiment, the siderophore is a mycobactin or an exochelin. In yet another embodiment, the growth regulatable rBCG is an auxotroph and wherein pantothenic acid is used to regulate growth of the auxotroph.

In another embodiment, the *Mycobacteria* major extracellular protein is from a *Mycobacteria* species selected from the group consisting of *Mycobacterium tuberculosis, Mycobacterium bovis, Mycobacterium leprae*, and *Mycobacterium avium* intracellulare. In another embodiment, the *Mycobacteria* major extracellular protein is a *Mycobacterium tuberculosis* major extracellular protein. In yet another embodiment, the *Mycobacteria* major extracellular protein is the 30 kDa protein.

In another embodiment, the growth regulatable rBCG further expresses at least one cytokine selected from the group consisting of interferon gamma, interleukin-2, interleukin-12, interleukin-4 receptor and granulocyte macrophage colony stimulating factor, and combinations thereof.

In one embodiment of the present invention, an immunogenic composition is provided comprising a rBCG expressing at least one *Mycobacteria* major extracellular protein selected from the group consisting of the 12 kDa protein, 14 kDa protein, 16 kDa protein, 23.5 kDa protein, 24 kDa protein, 30 kDa protein, 32A kDa protein, 32B kDa protein, 45 kDa protein, 58 kDa protein, 71 kDa protein, 80 kDa protein, and 110 KD protein, wherein the *Mycobacteria* major extracellular proteins are over-expressed and secreted; the rBCG is an auxotroph; and pantothenic acid is used to regulate growth of the auxotroph.

In another embodiment of the present invention, an immunogenic composition is provided comprising a rBCG expressing at least one *Mycobacteria* major extracellular protein selected from the group consisting of the 12 kDa protein, 14 kDa protein, 16 kDa protein, 23.5 kDa protein, 24 kDa protein, 30 kDa protein, 32A kDa protein, 32B kDa protein, 45 kDa protein, 58 kDa protein, 71 kDa protein, 80 kDa protein, and 110 KD protein, wherein the *Mycobacteria* major extracellular proteins are over-expressed and secreted; the rBCG is siderophore-dependent; and mycobactin is used to allow growth of the rBCG in vitro.

In one embodiment of the present invention, an immunogenic composition is provided comprising a growth regulatable recombinant attenuated intracellular pathogen expressing at least one major extracellular protein of an intracellular pathogen wherein the major extracellular protein is over-expressed.

In one embodiment of the present invention, an immunogenic composition is provided comprising a growth regulatable recombinant attenuated intracellular pathogen wherein the growth regulatable recombinant attenuated intracellular pathogen expresses at least one major extracellular protein of an intracellular pathogen wherein a nucleic acid sequence encoding for the at least one major extracellular protein is incorporated into the intracellular pathogen's chromosome(s) under a strong promoter such that the major extracellular protein is over-expressed.

In another embodiment, the growth regulatable recombinant attenuated intracellular pathogen is of the same species as the intracellular pathogen against which the immunogenic composition is directed. In another embodiment, the growth regulatable recombinant attenuated intracellular pathogen is of a different species than the intracellular pathogen against which the immunogenic composition is directed.

In another embodiment, the growth regulatable recombinant attenuated intracellular pathogen is selected from the group consisting of *Mycobacterium bovis, M. tuberculosis, M. leprae, M. kansasii, M. avium, Mycobacterium* sp., *Legionella pneumophila, L. longbeachae, L. bozemanii, Legionella* sp., *Rickettsia rickettsii, Rickettsia typhi, Rickettsia* sp., *Ehrlichia chaffeensis, Ehrlichia phagocytophila* geno group, *Ehrlichia* sp., *Coxiella bumetii, Leishmania* sp, *Toxpolasma gondii, Trypanosoma cruzi, Chlamydia pneumoniae, Chlamydia* sp, *Listeria monocytogenes, Listeria* sp, *Histoplasma* sp., *Francisella tularensis, Brucella* species, *Yersinia pestis, Bacillus anthracis*, and *Salmonella typhi.*

In another embodiment, the at least one major extracellular protein is from an intracellular pathogen selected from the group consisting of *Mycobacterium bovis, M. tuberculosis, M. leprae, M. kansasii, M. avium, Mycobacterium* sp., *Legionella pneumophila, L. longbeachae, L. bozemanii, Legionella* sp., *Rickettsia rickettsii, Rickettsia typhi, Rickettsia* sp., *Ehrlichia chaffeensis, Ehrlichia phagocytophila* geno group, *Ehrlichia* sp., *Coxiella bumetii, Leishmania* sp, *Toxpolasma gondii, Trypanosoma cruzi, Chlamydia pneumoniae, Chlamydia* sp, *Listeria monocytogenes, Listeria* sp,

*Histoplasma* sp., *Francisella tularensis, Brucella* species, *Yersinia pestis, Bacillus anthracis*, and *Salmonella typhi.*

In one embodiment of the present invention, an immunogenic composition is provided comprising a growth regulatable siderophore-dependent rBCG having a extrachromosomal nucleic acid sequence comprising a gene encoding for the 30 kDa *Mycobacteria* major extracellular protein wherein mycobactin is used to allow growth of the rBCG in vitro and wherein the 30 kDa *Mycobacteria* major extracellular protein is over expressed and secreted. In another embodiment, the growth regulatable siderophore-dependent rBCG further comprises an extrachromosomal nucleic acid sequence encoding for interferon gamma.

In one embodiment of the present invention, an immunogenic composition is provided comprising a growth regulatable siderophore-dependent rBCG wherein the growth regulatable rBCG expresses the 30 kDa *Mycobacteria* major extracellular protein and a nucleic acid sequence encoding for the 30 kDa *Mycobacteria* major extracellular protein is incorporated into the intracellular pathogen's chromosome(s) under a strong promoter such that the 30 kDa *Mycobacteria* major extracellular protein is over-expressed and wherein mycobactin is used to allow growth of the rBCG in vitro. In another embodiment, the growth regulatable siderophore-dependent rBCG further expresses interferon gamma.

DEFINITION OF TERMS

Figure 1:
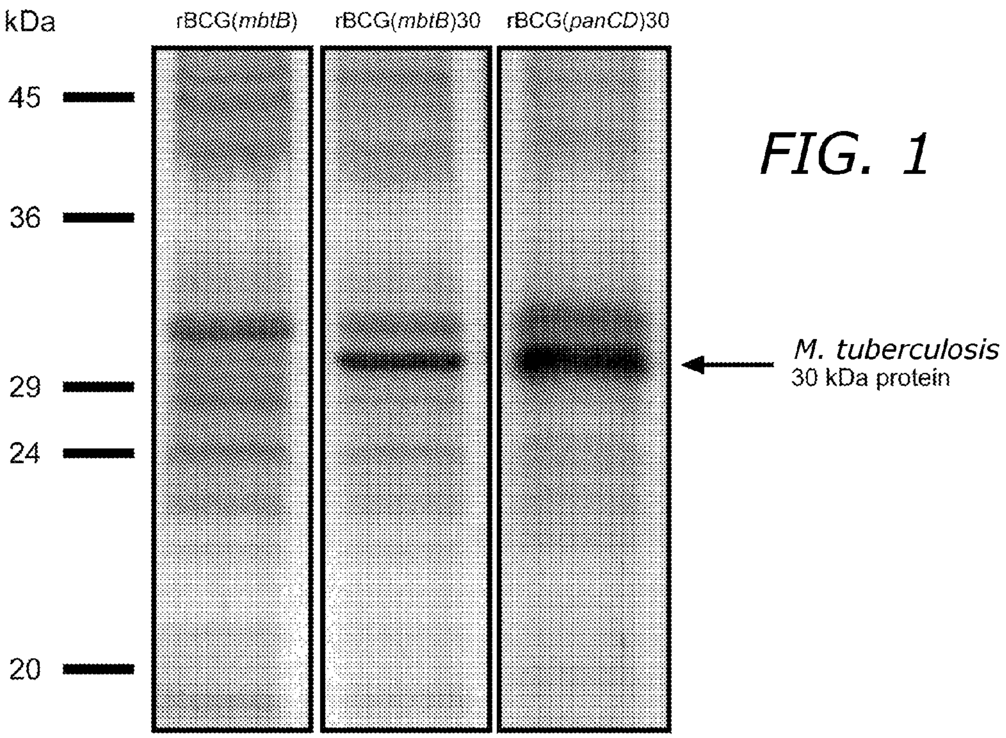
FIG. 1 depicts expression and secretion of the *M. tuberculosis* 30 kDa major secretory protein by rBCG(panCD)30 (pNBV1-30) Tice [Abbreviated as rBCG(panCD)30] and rBCG(mbtB)30 II (pNBV1-30) Tice [Abbreviated as rBCG (mbtB)30] according to the teachings of the present invention. rBCG(mbtB) is a recombinant BCG that does not express the *M. tuberculosis* 30 kDa major secretory protein

To facilitate an understanding of the following Detailed Description, Examples and appended claims it may be useful to refer to the following definitions. These definitions are non-limiting in nature and are supplied merely as a convenience to the reader.

Auxotroph or auxotrophic: As used herein "auxotroph" refers to a microorganism having a specific nutritional requirement not required by the wild-type organism. In the absence of the required nutrient the auxotroph will not grow whereas the wild-type will thrive.

Gene: A "gene" as used herein refers to at least a portion of a genetic construct having a promoter and/or other regulatory sequences required for, or that modify the expression of, the genetic construct.

Genetic Construct: A "genetic construct" as used herein shall mean a nucleic acid sequence encoding for at least one major extracellular protein from at least one intracellular pathogen. In one embodiment of the present invention the genetic construct is extrachromosomal DNA.

Growth Limited: As used herein, "growth limited" refers to a metabolically impaired form of the present invention's immunogenic compositions wherein the growth of the composition in the host is limited by the amount of a required nutrient pre-loaded into the composition in vitro. The growth limited compositions of the present invention are also referred to as growth-restricted.

Growth Regulatable: As used herein the term "growth regulatable" refers to an auxotrophic or metabolically impaired form of the present invention's immunogenic compositions. In the case of auxotrophs, growth is regulated by providing a nutrient essential for the auxotroph's growth at a concentration sufficient to induce growth. In the case of the metabolically impaired siderophore-dependent rBCG, growth is regulated by supplying iron and a siderophore in vitro thereby preloading the rBCG with iron. The amount of subsequent growth in vivo is dependent upon the amount of iron-loading that took place during in vitro growth, which in turn is dependent upon the amount of iron and siderophore provided during in vitro growth.

Host: As used herein "host" refers to the recipient of the present immunogenic compositions. Exemplary hosts are mammals including, but not limited to, primates, rodents, cows, horses, dogs, cats, sheep, goats, pigs and elephants. In one embodiment of the present invention the host is a human. For the purposes of this disclosure host is synonymous with "vaccinee."

Immunogen: As used herein the term "immunogen" shall mean any substrate that elicits an immune response in a host. Immunogens of the present invention include, but are not limited to major extracellular proteins, and their recombinant forms, derived from intracellular pathogens, such as, but not limited to members of the genus *Mycobacterium.*

Immunogenic Composition: An "immunogenic composition" as used herein comprises a recombinant vector, with or without an adjuvant, such as an intracellular pathogen, that expresses and/or secretes an immunogen in vivo and wherein the immunogen elicits an immune response in the host. The immunogenic compositions disclosed herein may be prototrophic, auxotrophic or metabolically impaired transformants. The immunogenic compositions of the present invention may or may not be immunoprotective or therapeutic. When the immunogenic compositions of the present invention prevent, ameliorate, palliate or eliminate disease from the host then the immunogenic composition may optionally be referred to as a vaccine. However, the term immunogenic composition is not intended to be limited to vaccines.

Major extracellular protein: As used herein, the term "major extracellular protein" is synonymous with "major secretory protein." Such proteins include proteins that are secreted using a classical secretion system as well as those released from the organism into its extracellular milieu by nonclassical or even unknown means. The present inventors have previously described and characterized the mycobacterial major extracellular proteins of the present invention. The descriptions and characterization of the present major extracellular proteins can be found, without limitation, in United States patent number 6,599,510, issued Jul. 29, 2003, the entire contents of which are hereby incorporated by reference.

Metabolically impaired: As used herein "metabolically impaired" shall mean a recombinant expression vector, specifically a recombinant Bacille Calmette Guérin (rBCG), that has an altered or deleted gene that is essential for normal metabolism. In the present case, the metabolic alteration results in a rBCG that cannot acquire iron and divide in vivo unless the rBCG is preloaded with iron during in vitro growth prior to the rBCG being administered in vivo. The organism is preloaded with iron by being cultured in vitro in the presence of a large amount of iron and siderophore; however, the amount of iron it can store is sufficient for it to multiply only a few generations in the host.

Nucleic Acid Sequence: As used herein the term "nucleic acid sequence" shall mean any continuous sequence of nucleic acids.

Prototrophic: As used herein "prototrophic" refers to a rBCG that does not require any substance in its nutrition additional to those required by the wild-type.

Transformant: As used herein a "transformant" refers to a microorganism that has been transformed with at least one heterologous or homologous nucleic acid encoding for a polypeptide that is expressed and/or secreted. In one embodiment of the present invention the transformant is BCG.

DETAILED DESCRIPTION OF THE INVENTION

The present invention provides methods for producing recombinant immunogenic compositions for preventing or treating diseases of intracellular pathogens in humans and animals, immunogenic compositions against diseases of intracellular pathogens in humans and animals, and a new approach to producing immunogenic composition against tuberculosis, leprosy, other mycobacterial diseases, and other intracellular pathogens.

Embodiments of the present invention are useful for preventing infection caused by intracellular pathogens such as, but not limited to, *Mycobacterium tuberculosis*, the agent of tuberculosis, infection by other pathogenic strains of *Mycobacteria* in humans and/or animals including *Mycobacterium bovis* and *Mycobacterium leprae*; and infection by intracellular pathogens in general.

A safe and effective vaccine against *M. tuberculosis* that is more potent than the currently available vaccine is sorely needed. The only currently available vaccine, *Mycobacterium bovis* strain Bacille Calmette Guérin (BCG), is of variable efficacy. Many studies have failed to demonstrate significant protection. One large carefully conducted meta-analysis has estimated the potency of BCG to be approximately 50%. Hence, a vaccine that improved the potency of BCG by even a small amount could have a tremendous impact on disease incidence.

The present inventors have previously disclosed recombinant BCG immunogenic compositions (rBCG30) expressing and secreting the *M. tuberculosis* 30 kDa major secretory protein (Horwitz et al. Proc. Natl. Acad. Sci. USA 97:113853-13858, 2000, which is incorporated by reference herein for all it contains regarding rBCG immunogenic compositions). These immunogenic compositions were more potent than BCG in the highly relevant guinea pig model. One of these immunogenic compositions, rBCG30 Tice I (pSMT3-MTB30) is used in the studies described below.

The present invention provides recombinant BCG immunogenic compositions that a) are growth-limited and/or growth-regulatable and b) are growth-limited and/or growth-regulatable and secrete a *M. tuberculosis* major extracellular protein, in one non-limiting example, the *M. tuberculosis* 30 kDa major secretory protein.

In one embodiment of the present invention, immunogenic compositions are provided comprising a rBCG wherein the rBCG is metabolically impaired and wherein a siderophore and iron are used to regulate growth of the metabolically impaired strain. This rBCG has been rendered siderophore-dependent and iron-loadable. It can be grown in vitro in the presence of iron and a siderophore such as, but not limited to, mycobactin J or exochelin, and thereby loaded with iron. Subsequently, when administered to the host, it can use the stored iron to multiply for several generations. As some growth of a live vaccine in the host is necessary to induce a strong protective immune response, the capacity of the rBCG to divide several times in the host allows the generation of a strong protective immune response. At the same time, the limited capacity of the rBCG to multiply in the host, as a result of its inability to acquire iron in the host, renders it unable to cause disseminated disease in the immunocompromised host and therefore safer than BCG. The rBCG(mbtB)30 immunogenic composition, while safer than BCG because it can not disseminate in an immunocompromised host, is also more potent than BCG.

In another embodiment, growth regulatable recombinant BCG immunogenic compositions, which can not grow more than a few generations in the host without a nutritional supplement, are designed to be safer than BCG, because unlike BCG, such immunogenic composition can not disseminate in the host in the absence of the nutritional supplement. In the present application, growth-regulatable auxotrophic recombinant BCG immunogenic compositions are provided that are dependent upon small amounts of the vitamin pantothenate. The rBCG can be administered to the host without providing a nutrient supplement to the host, in which case it can only undergo a limited number of divisions using stored nutrient but a sufficient number of divisions to generate a potent protective immune response. Alternatively, the vaccine can be administered to the host and the host provided a large amount of the nutrient, which can be given safely and inexpensively to mammals in large quantities, facilitating its acquisition by the live recombinant immunogenic composition in the host. In a non-limiting embodiment, the nutrient is the vitamin pantothenate. Under such circumstances, the immunogenic composition can persist longer in the host and induce a stronger protective immune response. Should the vaccine begin to disseminate and cause illness the nutrient supplement can be readily terminated, thereby stopping growth of the organism in the host and preventing serious disease. The amount of pantothenate normally present in the host eating a normal diet is orders of magnitude less than that needed to provide sufficient pantothenate for the growth of the rBCG. One version of the novel live recombinant pantothenate-dependent BCG immunogenic composition over-expresses the *M. tuberculosis* 30 kDa major secretory protein.

Embodiments of the present invention therefore provide recombinant strains of BCG Tice that are growth-limited and/or growth-regulatable including strains that secrete pathogen major extracellular proteins including *M. tuberculosis* major extracellular proteins.

The immunogenic compositions of the present invention are administered intradermally or by another route, e.g. subcutaneously, intranasally, inhaled, or even orally to a mammalian host. The immunogenic compositions are suitable for both immunocompetent and immunocompromised hosts. The immunogenic compositions induce a strong cell-mediated immune response to pathogen antigens in the vaccine. The immunogenic compositions subsequently protect the mammalian hosts against infection with *M. tuberculosis, Mycobacterium leprae, Mycobacterium avium*, other *Mycobacteria*, and other intracellular pathogens.

Additionally, the current commercially available BCG vaccine against tuberculosis is of limited efficacy against pulmonary tuberculosis. The immunogenic compositions of the present invention are more potent than the current commercially available vaccine in protecting against pulmonary tuberculosis and dissemination of bacteria to the spleen and other organs. Additionally, the immunogenic compositions of the present invention are safer than the current commercially available vaccine in that the immunogenic compositions are unable to disseminate in the immunocompromised host.

In one embodiment, the immunogenic compositions use extrachromosomal nucleic acids to express at least one recombinant immunogenic antigen gene and placing this gene(s) under the control of a strong promoter, preferably protein-specific promoter sequences. In another embodiment, the immunogenic composition comprises recombinant organisms expressing at least one recombinant immunogenic antigen gene from nucleic acid sequences integrated into the immunogenic composition's genomic DNA. As a result, intracellular pathogen immunogenic compositions having surprisingly superior specificity and potency than existing subunit or attenuated intracellular pathogen immunogenic compositions are provided.

Promoters useful for regulating the expression of genes in the immunogenic compositions of the present invention include a variety of promoters well known to persons or ordinary skill in the art. Particularly useful are strong promoters. The term "strong promoter" refers to a promoter that allows expression of the protein at a level at least as great as the level of the endogenous protein and preferably several times greater. Non-limiting examples of suitable strong promoters include, the promoter for rrs (also known as rrnS, MTB000019 and the 16S ribosomal RNA gene) both in full-length and shortened forms; the promoter for fbpB, the 30 kDa mycolyl transferase; the promoter for glnA1, the glutamine synthetase GlnA1 protein; the promoter for pknH, also known as Rv1266c; and the promoter for heat shock protein 60 also known as groEL2. These promoters can be used to regulate expression of extrachromosomal nucleic acid sequences or nucleic acid sequences integrated into the recombinant organism's genome. In one embodiment, the promoter is not a heat shock promoter or a stress protein promoter.

The technology described herein for enhancing the immune response of the host is applicable to other vaccines against intracellular pathogens such as vaccines or immunogenic compositions against *Francisella tularensis, Chlamydia species, Listeria monocytogenes, Brucella* species, *Yersinia pestis, Bacillus anthracis, Salmonella typhi, Leishmania* species, *Mycobacteria* species, *Trypanosoma cruzi, Toxoplasma gondii, Histoplasma capsulatum, Riskettsia* species, *Coxiella burnetii, Plasmodia* species that cause malaria, and Human Immunodeficiency Virus (HIV).

Furthermore, the recombinant immunogenic antigens over-expressed by the immunogenic compositions disclosed herein can be from species including, but not limited to, *Mycobacterium bovis, M. tuberculosis, M. leprae, M. kansasii, M. avium, Mycobacterium* sp., *Legionella pneumophila, L. longbeachae, L. bozemanii, Legionella* sp., *Rickettsia rickettsii, Rickettsia typhi, Rickettsia* sp., *Ehrlichia chaffeensis, Ehrlichia phagocytophila* geno group, *Ehrlichia* sp., *Coxiella bumetii, Leishmania* sp., *Toxpolasma gondii, Trypanosoma cruzi, Chlamydia pneumoniae, Chlamydia* sp., *Listeria monocytogenes, Listeria* sp., *Francisella tularensis, Bacillus anthracis*, and *Histoplasma* sp.

Suitable recombinant immunogenic antigens include the major extracellular proteins of *Mycobacteria* species including, but not limited to, the 12 kDa protein, 14 kDa protein, 16 kDa protein, 23 kDa protein, 23.5 kDa protein, 30 kDa protein, 32A kDa protein, 32B kDa protein, 45 kDa protein, 58 kDa protein, 71 kDa protein, 80 kDa protein, and 110 kDa protein and combinations thereof.

Growth-regulatable or growth-limited vaccines against other intracellular pathogens can be generated using the methods of the present invention. In a non-limiting example, the pathogen *Francisella tularensis* subspecies *tularensis* causes the disease tularemia. A vaccine called the Live Vaccine Strain (LVS), an attenuated version of a different subspecies of *F. tularensis*, has been developed. However, LVS can cause serious illness in humans requiring antibiotic treatment. Furthermore, it is not highly efficacious. Since, like BCG, *F. tularensis* has a siderophore that it requires to acquire iron, it can be rendered siderophore-dependent by knocking out a gene required for siderophore synthesis. Such a siderophore-dependent LVS strain can be grown in vitro in the presence of a siderophore and iron. However, it will not be able to acquire iron in the host where the siderophore is absent and therefore would not be able to multiply more than a few generations in the host and not be able to cause illness. Moreover, the siderophore-dependent strain can be engineered to over-express major extracellular proteins of *F. tularensis*, e.g. catalase-peroxidase or IglC proteins that have been shown to induce protective immunity against *F. tularensis* when provided via a subunit vaccine in adjuvant or when provided by recombinant attenuated *Listeria monocytogenes* expressing these proteins. Thus, the siderophore-dependent LVS would be a potent immunoprotective vaccine.

1. BCG Mutant Defective in Pantothenate Biosynthesis rBCG(panCD) Tice: A BCG mutant defective in pantothenate biosynthesis (pantothenate auxotroph) was constructed by disrupting the BCG Tice panCD genes via allelic exchange. The allelic exchange substrate was generated using a cloning strategy in which a panCD locus with a 1.3 kb deletion was created with an apramycin resistance ($apr^r$) gene inserted at the site of the deletion. This mutated allele was cloned into the allelic exchange vector phEX1 (a derivative of phAE87 [Bardarov et al., Microbiol. 148:3007-3017, 2002]) to generate phEX1 ΔpanCD::$apr^r$. This plasmid was electroporated into *Mycobacterium smegmatis* to generate the specialized transducing phage. BCG Tice was infected with this purified phage and then plated on 7H10 plates containing 50 μg $mL^{-1}$ apramycin and 50 μg $mL^{-1}$ calcium D-pantothenate to select for clones that had undergone a homologous recombination event. Four apramycin resistant clones were obtained of which two were shown to be pantothenate auxotrophs. No growth was observed for the auxotrophs on plates or in broth without the addition of calcium D-pantothenate. In broth culture, the mutant strain grows at a rate similar to the wild-type strain in the presence of ≧10 μg $mL^{-1}$ calcium D-pantothenate. To ensure a pure culture, one of the pantothenate auxotrophic clones was plated at low density and a single colony was reisolated. The strain name is abbreviated as rBCG(panCD).

2. BCG Mutant Defective in Pantothenate Biosynthesis Expressing and Secreting the *M. tuberculosis* 30 kDa Major Secretory Protein rBCG(panCD)30 (pNBV1-30) Tice: A BCG mutant defective in pantothenate biosynthesis that also expresses and secretes the *M. tuberculosis* 30 kDa major secretory protein was constructed by electroporating the plasmid pNBV1-30 ($hyg^r$) into rBCG(panCD) and selecting transformants on 7H11 agar with 50 μg $mL^{-1}$ hygromycin, 50 μg $mL^{-1}$ apramycin, and 50 μg $mL^{-1}$ pantothenate. The plasmid pNBV1-30 was constructed by cloning approximately 1.5 kb of DNA containing the coding region of the *M. tuberculosis* 30 kDa major secretory protein gene (fbpB) and approximately 500 bp of sequence upstream of the start codon into the multi-cloning site of pNBV1 (Howard et al. Gene 166:181-182, 1995). A single hygromycin and apramycin resistant clone was cultured in 7H9 medium containing 0.01% (w/v) tyloxapol, 50 μg $mL^{-1}$ hygromycin, and 50 μg $mL^{-1}$ pantothenate. The clone was found to express and export a high level of recombinant *M. tuberculosis* 30 kDa major secretory protein as determined by polyacrylamide gel electrophoresis (FIG. 1). The strain stably expressed and exported the 30 kDa major secretory protein even in the absence of the selective antibiotic hygromycin for at least ~40 generations (4 subcultures, 1:1000 dilutions). The strain name is abbreviated as rBCG (panCD)30.

3. BCG Mutant Defective in Iron Acquisition Expressing and Secreting the *M. tuberculosis* 30 kDa Major Secretory Protein rBCG(mbtB)30 II (pNBV1-30) Tice: A BCG mutant defective in iron acquisition that also expresses and secretes the *M. tuberculosis* 30 kDa major secretory protein was constructed by electroporating the plasmid pNBV1-30 ($hyg^r$) into rBCG(mbtB) (also known as rBCG-mbtB) and selecting transformants on 7H10 agar with 50 μg $mL^{-1}$ hygromycin and 1 μg $mL^{-1}$ mycobactin J. Eight individual hygromycin resistant clones were randomly selected and screened for expression and export of recombinant *M. tuberculosis* 30 kDa major secretory protein by polyacrylamide gel electrophoresis. All eight clones were found to express and export a high level of the 30 kDa protein. The strain stably expressed and exported the 30 kDa major secretory protein even in the absence of the selective antibiotic hygromycin for at least ~50 generations (5 subcultures, 1:1000 dilutions). One such clone is shown in FIG. 1. The strain name is abbreviated as rBCG (mbtB)30.

4. BCG Mutant Defective in L-Tryptophan Biosynthesis Expressing and Secreting the *M. tuberculosis* 30 kDa Major Secretory Protein rBCG(trpD)30 (pSMT3-MTB30) Tice: A BCG mutant defective in L-tryptophan biosynthesis that also expresses and secretes the *M. tuberculosis* 30 kDa major secretory protein was constructed by electroporating the plasmid pSMT3-MTB30 ($hyg^r$) into the L-trypthophan auxotroph strain rBCG(trpD) (also known as BCG Tice trpD) and selecting transformants on 7H11 agar with 50 μg $mL^{-1}$ hygromycin, 50 μg $mL^{-1}$ kanamycin, and 50 μg $mL^{-1}$ L-tryptophan. Ten individual hygromycin and kanamycin resistant clones were randomly selected and screened for expression and export of recombinant *M. tuberculosis* 30 kDa major secretory protein by polyacrylamide gel electrophoresis by polyacrylamide gel electrophoresis and immunoblotting with polyvalent, highly specific rabbit anti-30 kDa protein immunoglobulin. The strain was found to produce ~10-20 times more 30 kDa antigen per mL of culture than a control BCG Tice strain. The strain name is abbreviated as rBCG(trpD)30.

5. Recombinant BCG Immunogenic Compositions Co-Expressing Host Immunostimulatory Cytokines and *M. tuberculosis* Major Extracellular Proteins Previously, it was known that the immunostimulatory cytokines interleukin 2 (IL-2), interleukin 12 (IL-12), granulocyte-macrophage colony stimulating factor (GM-CSF) and interferon gamma (INFγ) are associated with enhanced cell-mediated immunity against intracellular pathogens including *Mycobacterium tuberculosis*. For example, IL-12 enhances the resistance of mice to *M. tuberculosis* and mice lacking interferon gamma show increased susceptibility to *M. tuberculosis*. These immunostimulatory cytokines, when present in close proximity to the *M. tuberculosis* 30 kDa major secretory protein or other *M. tuberculosis* major extracellular proteins can enhance the protective immune response against tuberculosis induced by the extracellular proteins. Moreover, a recombinant BCG immunogenic composition co-expressing one of these immunostimulatory cytokines and the 30 kDa major secretory protein or other *M. tuberculosis* major extracellular proteins induces greater protective immunity than a recombinant BCG vaccine expressing the extracellular protein in the absence of the immunostimulatory protein.

Previous studies have shown that immunostimulatory cytokines, e.g. IL-2 and IL-12, can augment the efficiency of subunit vaccines (Baldwin et al. Infect. Immun. 66:2951-2959, 1998). However, none of the previously reported subunit vaccines have approached the efficacy of BCG.

Recombinant BCG expressing various murine and human cytokines have previously been reported (Murray et al. Proc. Natl. Acad. Sci. USA 93:934-939, 1996; O'Donnell et al. Infect. Immun. 62:2508-2514, 1994). However, such cytokine-producing recombinant BCG vaccines did not induce more potent protection in animal models than rBCG alone. The present inventors have determined that a recombinant BCG vaccine expressing only interferon gamma was not more potent than the parent BCG strain. Surprisingly, the recombinant BCG co-expressing interferon gamma and the 30 kDa *M. tuberculosis* major secretory protein was more potent than rBCG30, the strain only expressing the 30 kDa protein. Thus, when expressed by BCG, interferon gamma did not enhance the level of protective immunity conferred by BCG alone, but when expressed by rBCG30, it did enhance the level of protective immunity conferred by rBCG30 alone. Therefore, the present inventors have determined that the co-expression of a majorly abundant extracellular antigen from an intracellular pathogen and a cytokine will result in enhanced protective immunity.

The present invention provides recombinant BCG immunogenic compositions expressing cytokines including, but not limited to, interleukin-2 (IL-2), interleukin-10 (IL-10), interleukin-12 (IL-12), interleukin-4 (IL-4), interleukin-6 (IL-6), interleukin-7 (IL-7), interleukin-8 (IL-8), interleukin-15 (IL-15), interleukin-18 (IL-18), interferon gamma, tumor necrosis factor alpha (TNF-alpha), granulocyte macrophage colony stimulating factor (GM-CSF). The human cytokines IL-2, IL-12, and GM-CSF have been reported to be active in the guinea pig and active in non-glycosylated form. Additionally, rBCGs expressing cytokine receptors such as, but not limited to, the soluble IL-4 receptor (sIL4R) and the receptors for IL-2, IL-4, IL-7, IL-12, IFNs, GM-CSF or TNF-alpha are disclosed.

T lymphocytes are a major source of cytokines. These cells bear antigen specific receptors on their cell surface to allow recognition of foreign pathogens. They can also recognize normal tissue during episodes of autoimmune diseases. There are two main subsets of T lymphocytes, distinguished by the presence of cell surface molecules known as CD4 and CD8. T lymphocytes expressing CD4 are also known as helper T cells, and these are regarded as being the most prolific cytokine producers. This subset can be further subdivided into TH1 and TH2, and the cytokines they produce are known as TH1-type cytokines and TH2-type cytokines.

TH1-type cytokines tend to produce the proinflammatory responses responsible for killing intracellular parasites and for perpetuating autoimmune responses. Interferon gamma is the main TH1 cytokine. Excessive proinflammatory responses can lead to uncontrolled tissue damage, so there needs to be a mechanism to counteract this. The TH2-type cytokines include interleukins 4, 5, and 13, which are associated with the promotion of IgE and eosinophilic responses in atopy, and also interleukin-10, which has more of an anti-inflammatory response. In excess, TH2 responses will counteract the TH1 mediated microbicidal action. The optimal scenario would therefore seem to be that humans should produce a well balanced TH1 and TH2 response, suited to the immune challenge.

Many researchers regard allergy as a TH2 weighted imbalance, and recently immunologists have been investigating ways to redirect allergic TH2 responses in favor of TH1 responses to try to reduce the incidence of atopy. Some groups have been looking at using high dose exposure to allergen to drive up the TH1 response in established disease, and other groups have been studying the use of mycobacterial vaccines in an attempt to drive a stronger TH1 response in early life.

While a TH1 type of immune response is thought to promote immunoprotection against intracellular pathogens including *M. tuberculosis*, a TH2 type of immune response may be counterproductive. A shift towards a TH2 type response and cytokine profile has been found in tuberculosis patients. Based on the evidence that the soluble (extracellular) portion of the human interleukin 4 receptor can bind to interleukin 4 (IL-4) and the description of its molecular structure, a recombinant immunogenic composition expressing and secreting this soluble receptor fragment could competitively bind to circulating IL-4, significantly downmodulating the TH2 response to vaccine antigens, and shift the TH1 to TH2 ratio in favor of a TH1 response. Accordingly, to suppress a potential TH2 response to the antigens expressed by the immunogenic compositions of the present invention, a recombinant BCG expressing the IL-4 antagonist—soluble IL-4 Receptor (sIL4R) is contemplated.

Immunostimulatory rBCG immunogenic compositions comprising intracellular pathogen immunogenic antigens and cytokines are further disclosed in co-pending U.S. Provisional Patent Application No. 60/744,557 filed Apr. 10, 2006 and International Patent Application No. PCT/US2007/066350, filed on even date herewith, the contents of both of which are incorporated herein in their entirety.

Example 1

Figure 2:
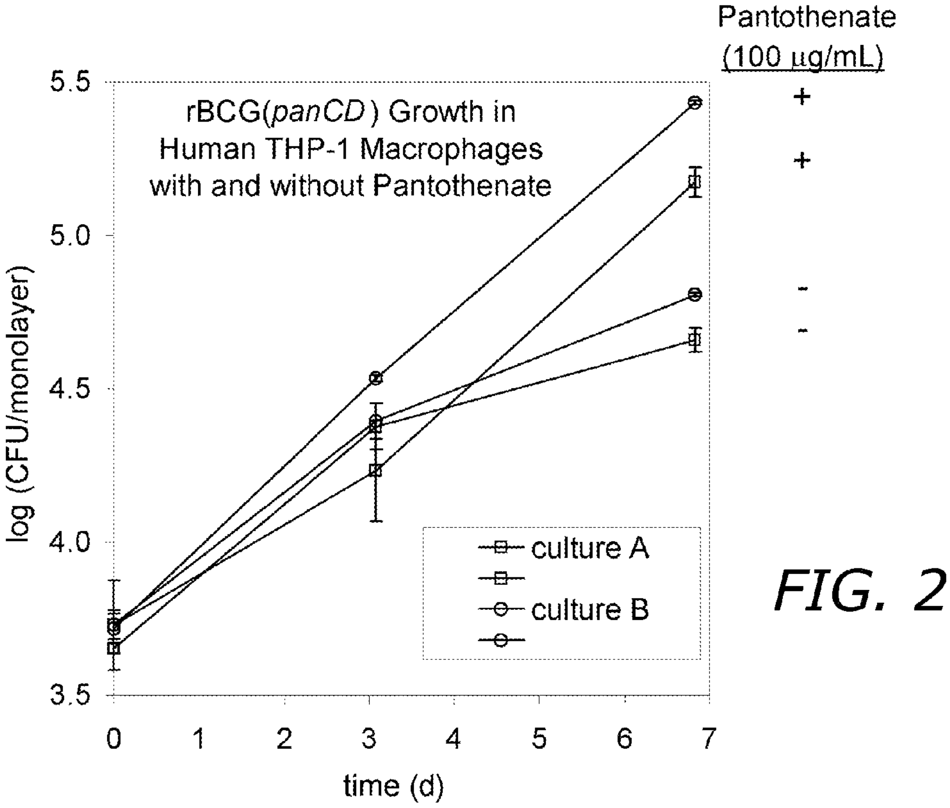
FIG. 2 depicts the growth of rBCG(panCD) in THP-1 cells in the presence and absence of pantothenate according to the teachings of the present invention.

Studies of Growth of Auxotrophic Strains in vitro: rBCG(panCD) and rBCG(panCD)30 (pNBV1-30) Tice The rBCG(panCD) and rBCG(panCD)30 strains are pantothenate (Vitamin B5) auxotrophs. In broth culture, rBCG (panCD) grew at a rate similar to the wild-type BCG strain in the presence of $\geqq 10$ μg $mL^{-1}$ pantothenate. rBCG(panCD) displayed less than maximal intracellular growth in human macrophages when macrophages were cultured in standard tissue culture medium which contains 0.25 μg $mL^{-1}$ pantothenate. Intracellular growth similar to the wild-type strain was achieved by adding an additional 100 μg $mL^{-1}$ pantothenate (0.42 mM) to the tissue culture medium (FIG. 2, culture A was grown with 50 μg $mL^{-1}$ pantothenate and culture B was grown with 500 μg $mL^{-1}$ pantothenate prior to infection of the macrophages).

Example 2

Figure 3:
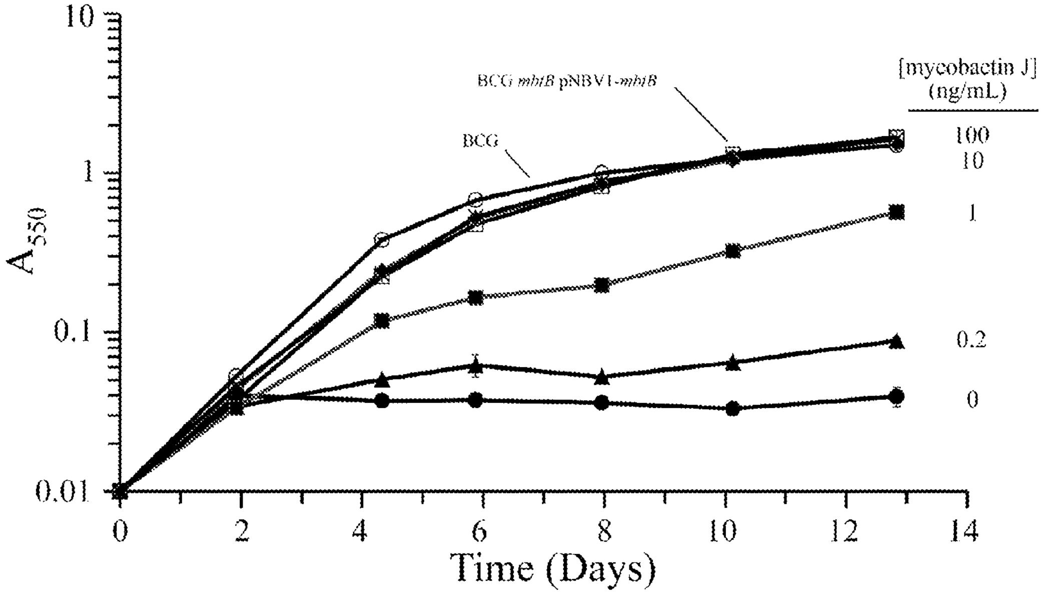
FIG. 3 depicts the growth of BCG, BCGmbtBpNBV1-mbtB, and rBCG(mbtB)30 in broth culture in the presence of different concentrations of mycobactin J according to the teachings of the present invention. BCG is represented by the open circles and BCGmbtBpNBV1-mbtB is represented by open squares. rBCG(mbtB)30 is represented by the closed symbols.
Figure 4:
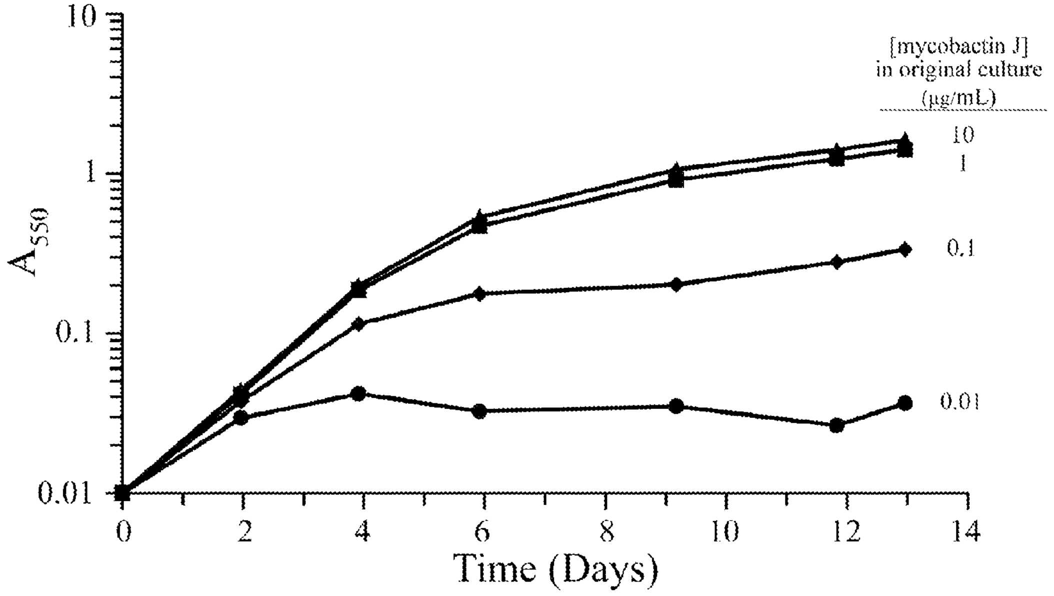
FIG. 4 depicts the residual growth of rBCG(mbtB)30 in broth culture lacking mycobactin J after growth in the presence of different concentrations of mycobactin J according to the teachings of the present invention.

Studies of Growth-Restricted Strains in vitro: rBCG(mbtB) and rBCG(mbtB)30 II (pNBV1-30) Tice The rBCG(mbtB)30 strain is mycobactin-dependent and thus it is defective in iron acquisition. Growth of the strain in broth is normal when supplemented with $\geqq 10$ ng/mL mycobactin J while growth is reduced at mycobactin J concentrations $\leqq 1$ ng/mL (FIG. 3). Although rBCG(mbtB)30 is dependent on exogenous mycobactin for growth, the strain can multiply for a limited number of generations after removal of mycobactin (FIG. 4). The number of generations of residual growth in the absence of mycobactin is dependent upon the level of mycobactin in the medium in which the strain was initially grown. When initially grown in broth supplemented with a high concentration of mycobactin J (10 μg/mL) and the cells washed, the strain is capable of approximately 10 generations of growth after subculture into medium lacking mycobactin J. When initially grown in broth supplemented with a low concentration of mycobactin J (0.01 μg/mL) and the cells washed, the strain is capable of only approximately 2 generations of growth after subculture into medium lacking mycobactin J.

Figure 5:
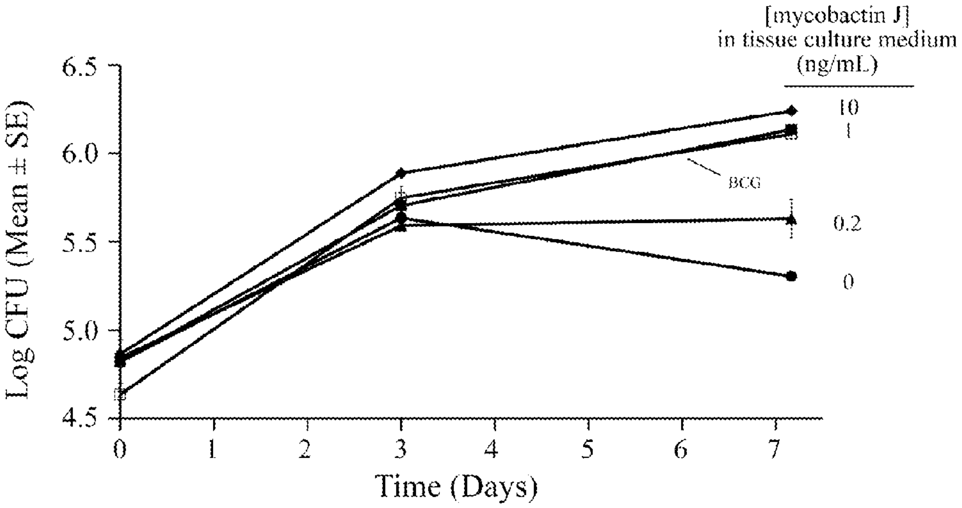
FIG. 5 depicts the intracellular growth of BCG and rBCG (mbtB)30 in THP-1 cells in the presence of different concentrations of mycobactin J according to the teachings of the present invention. BCG is represented by open squares and rBCG(mbtB)30 is represented by closed symbols.
Figure 6:
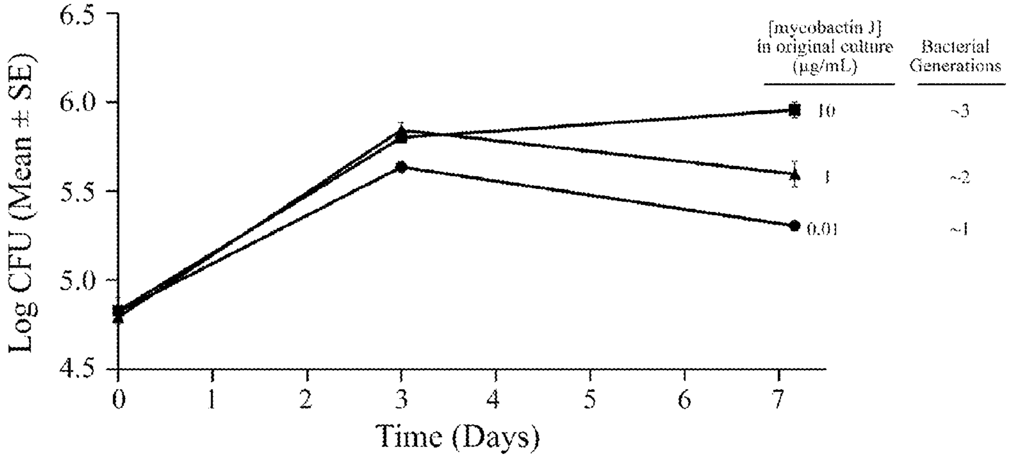
FIG. 6 depicts the residual intracellular growth of rBCG (mbtB)30 in THP-1 cells in the absence of mycobactin J after growth of rBCG(mbtB)30 in broth in the presence of different concentrations of mycobactin J according to the teachings of the present invention.

The capacity of rBCG(mbtB)30 for residual growth after the removal of mycobactin J was also tested in human THP-1 macrophages (FIG. 5). When the bacteria were initially grown in a low concentration of mycobactin J (0.01 μg/mL) and then added to THP-1 cells, there was marginal growth in the absence of mycobactin. Growth was normal, or nearly so, when the tissue culture medium was supplemented with $\geqq 1$ ng/mL of mycobactin J. The residual growth of rBCG(mbtB)30 in the absence of mycobactin was also evaluated in human THP-1 macrophages (FIG. 6). When grown in a low concentration of mycobactin J (0.01 μg/mL) prior to infection of THP-1 cells, rBCG(mbtB)30 displayed little net growth over the seven days infection period (equivalent to approximately 1 generation). When grown in a high concentration of mycobactin J (10 μg/mL) prior to infection of the THP-1 cells, rBCG(mbtB)30 multiplied approximately 1 log over the course of the infection (equivalent to ~3 generations).

Example 3

Survival Studies of Auxotrophic and Growth-Restricted Strains In Vivo

The studies of the survival of the auxotrophic and growth-limited vaccine strains utilized guinea pigs because the guinea pig model is especially relevant to human tuberculosis. Furthermore, the wild-type BCG vaccine is known to undergo multiplication in guinea pigs prior to containment by the guinea pig's immune system. Multiplication of the BCG vaccine may be required for optimal immunity against tuberculosis.

Aliquots were removed from logarithmically growing wild-type or recombinant BCG cultures, and the bacteria were pelleted by centrifugation at 3,500×g for 15 min. The bacteria were then washed with 1× phosphate buffered saline (1×PBS, 50 mM sodium phosphate pH 7, 150 mM sodium chloride) and resuspended in 1×PBS to the desired concentration. The immunization inoculum contained from $10^3$ to $10^7$ viable wild-type or recombinant BCG bacteria in a total volume of 100 μl.

Experiment 1

1. Immunization of Animals

Specific-pathogen free 250-300 g outbred male Hartley strain guinea pigs from Charles River Breeding Laboratories, in groups of 3, were immunized intradermally with $10^6$-$10^7$ CFU of one of the following strains of BCG:

Group A: BCG Tice Parental Control (BCG)

Group B: rBCG30 Tice I (pSMT3-MTB30)(rBCG30)

Group C: rBCG(trpD) Tice (rBCG(trpD))

Group D: rBCG(trpD)30 (pSMT3-MTB30) Tice (rBCG(trpD)30)

Group E: rBCG(trpD) Tice—Animals fed diet high in tryptophan (rBCG(trpD)-diet)

Group F: rBCG(trpD)30 (pSMT3-MTB30) Tice—Animals fed diet high in tryptophan (rBCG(trpD)30-diet)

Group G: rBCG(panCD) Tice (rBCG(panCD))

Group H: rBCG(panCD) Tice—Animals fed diet high in pantothenate (rBCG(panCD)-diet)

Group I: rBCG(mbtB) Tice—Grown in medium containing a low mycobactin J concentration (rBCG(mbtB) Lo Fe)

Group J: rBCG(mbtB) Tice—Grown in medium containing a high mycobactin J concentration (rBCG(mbtB) Hi Fe)

2. Survival of Vaccines in Guinea Pigs

Three weeks after immunization the animals were euthanized and the spleen of each animal was removed and cultured for colony forming units (CFU) of BCG on Middlebrook 7H11 agar containing 50 μg/mL L-tryptophan, 50 μg/mL pantothenate, and 0.1 μg/mL mycobactin J for three weeks at 37° C., 5% $CO_2$-95% air atmosphere. The results of the assay for CFU in the spleens are shown in Table 1. The limit of detection was 4 CFU (0.6 log CFU).

TABLE 1

Vaccine Survival in vivo - Experiment 1

| Group | Strain | Spleen (Mean Log CFU ± SE) |
|---|---|---|
| A | BCG | 2.8 ± 0.2 |
| B | rBCG30 | 3.9 ± 0.1 |
| C | rBCG(trpD) | 0.7 ± 0.1 |
| D | rBCG(trpD)30 | 0.7 ± 0.0 |
| E | rBCG(trpD)-diet | 1.3 ± 0.3 |
| F | rBCG(trpD)30-diet | 0.9 ± 0.2 |
| G | rBCG(panCD) | 0.7 ± 0.0 |
| H | rBCG(panCD)-diet | 0.9 ± 0.3 |
| I | rBCG(mbtB) Lo Fe | 1.3 ± 0.4 |
| J | rBCG(mbtB) Hi Fe | 1.9 ± 0.4 |

These results showed that animals immunized with BCG and rBCG30 had a relatively high level of BCG organisms (2.8 and 3.9 log CFU) in their spleens three weeks after immunization, while the animals immunized with the auxotrophic BCG vaccines had much lower levels of bacteria (0.7-1.9 log CFU) in their spleens, thus demonstrating a much higher degree of safety with these strains. In addition, there was evidence that supplementation of the guinea pigs diet with the nutrient required by the auxotrophic vaccine (L-tryptophan or pantothenate) resulted in greater survival of the auxotrophic strains (rBCG(trpD): 0.7 log CFU vs. rBCG(trpD)-diet: 1.3 log CFU; rBCG(trpD)30: 0.7 log CFU vs. rBCG(trpD)30-diet: 0.9 log CFU; rBCG(panCD): 0.7 log CFU vs. rBCG(panCD)-diet: 0.9 log CFU). The growth-limited vaccine, rBCG(mbtB), had greater survival in the spleen than the auxotrophic strains, but still less than BCG and rBCG30, demonstrating greater safety. Furthermore, survival was increased by growing the vaccine with a high mycobactin J concentration (iron loaded vaccine) prior to immunization (rBCG(mbtB) Lo Fe: 1.3 log CFU vs. rBCG(mbtB) Hi Fe: 1.9 log CFU) demonstrating that growth and/or survival of the growth-restricted strain rBCG(mbtB) can be controlled by changing the level of iron loading of the strain before immunization.

Example 4

Cell-Mediated, Humoral, and Protective Immunity Studies

The studies of the efficacy of the vaccines utilized guinea pigs because the guinea pig model is especially relevant to human tuberculosis clinically, immunologically, and pathologically. In contrast to the mouse and rat, but like the human, the guinea pig a) is susceptible to low doses of aerosolized *M. tuberculosis*; b) exhibits strong cutaneous delayed-type hypersensitivity (DTH) to tuberculin; and c) displays Langhans giant cells and caseation in pulmonary lesions. However, whereas only about 10% of immunocompetent humans who are infected with *M. tuberculosis* develop active disease over their lifetime (half early after exposure and half after a period of latency), infected guinea pigs always develop early active disease. While guinea pigs differ from humans in this respect, the consistency with which they develop active disease after infection with *M. tuberculosis* is an advantage in trials of vaccine efficacy.

Aliquots were removed from logarithmically growing wild-type or recombinant BCG cultures, and the bacteria were pelleted by centrifugation at 3,500×g for 15 min. The bacteria were then washed with 1× phosphate buffered saline (1×PBS, 50 mM sodium phosphate pH 7, 150 mM sodium chloride) and resuspended at a final concentration of 1×$10^4$ or 1×$10^7$ colony-forming units per ml in 1×PBS. The immunization inoculum contained $10^3$ or $10^6$ viable wild-type or recombinant BCG bacteria in a total volume of 100 μl.

Tyloxapol is included in the immunogenic compositions to allow solubilization of mycobactin J with the rBCG(mbtB) and rBCG(mbtB)30 vaccines. It was also added to BCG in some of these experiments as a control. Tyloxopol has no influence on protection.

Experiment 2

1. Immunization of Animals

Specific-pathogen free 250-300 g outbred male Hartley strain guinea pigs from Charles River Breeding Laboratories, in groups of 15 or 21, were sham-immunized by intradermal administration of buffer (15 animals total) or immunized intradermally with $10^3$ or $10^6$ CFU of one of the following strains of BCG (21 animals/group):

Group A: Sham-immunized (Sham)

Group B: $10^3$ BCG Tice Parental Control (BCG)

Group C: $10^3$ rBCG30 Tice I (pSMT3-MTB30)(rBCG30)

Group D: $10^3$ rBCG30/hINFγ (pSMT3-MTB30; pGB9.2-hINFγ) Tice (rBCG30/hINFγ)

Group E: $10^6$ rBCG(mbtB) Tice—Grown in medium containing a low mycobactin J concentration and 0.1% Tyloxapol (rBCG(mbtB) Lo Fe)

Group F: $10^6$ rBCG(mbtB) Tice—Grown in medium containing a high mycobactin J concentration and 0.1% Tyloxapol (rBCG(mbtB) Hi Fe)

Group G: $10^6$ rBCG(mbtB)30 II (pNBV1-30) Tice—Grown in medium containing a low mycobactin J concentration and 0.1% Tyloxapol (rBCG(mbtB)30 Lo Fe)

Group H: $10^6$ rBCG(mbtB)30 II (pNBV1-30) Tice—Grown in medium containing a high mycobactin J concentration and 0.1% Tyloxapol (rBCG(mbtB)30 Hi Fe)

2. Cutaneous Delayed-type Hypersensitivity (DTH) to Purified Recombinant *M. tuberculosis* 30 kDa Major Secretory Protein (r30)

Ten weeks after immunization, 6 guinea pigs in each group were shaved over the back and injected intradermally with 10 μg of purified recombinant *M. tuberculosis* 30 kDa major secretory protein (r30) in 100 μl phosphate buffered saline. After 24 h, the diameter of erythema and induration was measured. A separate group of animals from the one used in the challenge studies was used for skin-testing to eliminate the possibility that the skin test itself might influence the outcome. The results are summarized in Table 2.

TABLE 2

Cutaneous DTH - Experiment 2

| Group | Strain | Test Antigen | Erythema (mm ± SE) | Induration (mm ± SE) |
|---|---|---|---|---|
| A | Sham | r30 | 2.7 ± 1.3 | 0 ± 0 |
| B | BCG | r30 | 5.8 ± 1.4 | 0 ± 0 |
| C | rBCG30 | r30 | 11.8 ± 2.6 | 5.6 ± 3.5 |
| D | rBCG30/hINFγ | r30 | 6.3 ± 1.4 | 0 ± 0 |
| E | rBCG(mbtB) Lo Fe | r30 | 2.0 ± 1.0 | 0 ± 0 |
| F | rBCG(mbtB) Hi Fe | r30 | 3.0 ± 1.6 | 0 ± 0 |
| G | rBCG(mbtB)30 Lo Fe | r30 | 14.4 ± 2.3 | 3.6 ± 3.6 |
| H | rBCG(mbtB)30 Hi Fe | r30 | 10.3 ± 1.3 | 4.7 ± 2.1 |

These results showed that sham-immunized animals (Group A) and animals immunized with the parental BCG Tice strain (Group B) had no induration upon testing with r30. Similarly, animals immunized with a growth-limited vaccine [rBCG(mbtB)] not over-expressing the 30 kDa protein had no induration upon testing with r30, whether the vaccine was grown under high mycobactin J (Group F) or low mycobactin J (Group E) conditions. In contrast, animals immunized with a recombinant BCG strain over-expressing r30 (Group C) had induration in response to r30. Similarly, animals immunized with the growth-limited strain rBCG(mbtB)30, whether grown under high mycobactin J (Group H) or low mycobactin J (Group G) conditions, showed induration upon testing with r30. Interestingly, the recombinant BCG expressing both r30 and human interferon gamma did not show induration upon testing with r30, although it did display some erythema.

3. Protective Immunity to Aerosol Challenge

Ten weeks after immunization, the remaining animals in Groups A-H were challenged with an aerosol generated from a 10 ml single-cell suspension containing 7.5×$10^4$ CFU of *M. tuberculosis*. Prior to challenge, the challenge strain, *M. tuberculosis* Erdman strain (ATCC 35801), had been passaged through outbred guinea pigs to maintain virulence, cultured on 7H11 agar, subjected to gentle sonication to obtain a single cell suspension, and frozen at −70° C. This aerosol dose delivered ~10 live bacilli to the lungs of each animal. The airborne route of infection was used because this is the natural route of infection for pulmonary tuberculosis. A relatively large dose was used so as to induce measurable clinical illness in 100% of control animals within a relatively short time frame (10 weeks). Afterwards, guinea pigs were individually housed in stainless steel cages contained within a laminar flow biohazard safety enclosure and allowed free access to standard laboratory chow and water. The animals were observed for illness and weighed weekly for 10 weeks and then euthanized. The right lung and spleen of each animal was removed and cultured for CFU of *M. tuberculosis* on Middlebrook 7H11 agar for two weeks at 37° C., 5% $CO_2$-95% air atmosphere. The results of the assay for CFU in the lungs and spleens are shown in Table 3.

TABLE 3

CFU in Lungs and Spleens - Experiment 2

| Group | Strain | Lung (Mean Log CFU ± SE) | Spleen (Mean Log CFU ± SE) |
|---|---|---|---|
| A | Sham | 6.03 ± 0.10 | 5.57 ± 0.17 |
| B | BCG | 4.83 ± 0.12 | 4.20 ± 0.21 |
| C | rBCG30 | 4.04 ± 0.21 | 2.87 ± 0.23 |
| D | rBCG30/hINFγ | 3.57 ± 0.27 | 2.38 ± 0.30 |
| E | rBCG(mbtB) Lo Fe | 4.49 ± 0.19 | 3.69 ± 0.33 |
| F | rBCG(mbtB) Hi Fe | 4.68 ± 0.25 | 4.42 ± 0.24 |
| G | rBCG(mbtB)30 Lo Fe | 4.40 ± 0.28 | 3.17 ± 0.39 |
| H | rBCG(mbtB)30 Hi Fe | 4.42 ± 0.25 | 2.93 ± 0.31 |

These results showed that animals immunized with BCG or any recombinant BCG strain had much lower CFU in the lungs and spleens than the sham immunized animals.

Animals immunized with the recombinant BCG strain secreting both the *M. tuberculosis* 30 kDa major secretory protein and human interferon gamma (rBCG30/hINFγ) had markedly fewer CFU in the lung and spleen than even animals immunized with rBCG30; animals immunized with rBCG30/hINFγ had 0.5 logs fewer CFU in the lung and spleen than animals immunized with rBCG30. Moreover, in the case of animals immunized with rBCG30/hINFγ, 50% of the animals had no detectable CFU in their spleens and thus were scored at the limit of detection of 1.56 logs. In contrast, in the case of rBCG30 immunized animals, only 14% of the animals had no detectable CFU in the spleen. Compared with animals immunized with BCG, animals immunized with rBCG30/hINFγ had 1.3 logs fewer CFU in the lung and 1.8 logs fewer CFU in the spleen.

Furthermore, animals immunized with the growth-limited strain rBCG(mbtB) had fewer CFU in the lung than BCG, whether grown in high or low concentrations of mycobactin J before immunization. Remarkably, animals immunized with the growth-limited recombinant BCG strain over-expressing the *M. tuberculosis* 30 kDa major secretory protein [rBCG (mbtB)30], whether grown in the presence of high or low amounts of mycobactin J before immunization, showed an impressive reduction in CFU in animal organs compared with BCG. Animals immunized with rBCG(mbtB)30, whether grown in the presence of high or low amounts of iron before immunization, had 0.4 logs fewer CFU in the lungs than BCG-immunized animals; animals immunized with rBCG (mbtB)30 grown in a low amount of mycobactin J before immunization had 1.0 log fewer CFU in the spleen and animals immunized with rBCG(mbtB)30 grown in a high amount of mycobactin J before immunization had 1.3 log fewer CFU in the spleen than BCG-immunized animals. Remarkably, the reduction in CFU in the spleen in animals immunized with rBCG(mbtB)30 grown in a high amount of mycobactin before immunization was comparable to that observed with rBCG30, which is not growth-limited.

Experiment 3

1. Immunization of Animals

Specific-pathogen free 250-300 g outbred male Hartley strain guinea pigs from Charles River Breeding Laboratories, in groups of 6, were sham-immunized by intradermal administration of buffer or immunized intradermally with $10^3$ or $10^6$ CFU of one of the following strains of BCG:

Group A: Sham-immunized (Sham)

Group B: $10^3$ BCG Tice Parental Control (BCG)

Group C: $10^3$ rBCG30 Tice I (pSMT3-MTB30) (rBCG30)

Group D: $10^3$ rBCG30/hINFγ (pSMT3-MTB30; pGB9.2-hINFγ) Tice (rBCG30/hINFγ)

Group E: $10^3$ rBCG30/hGM-CSF(pSMT3-MTB30; pGB9.2-hGM-CSF) Tice (rBCG30/hGM-CSF)

Group F: $10^3$ rBCG30/hIL-2 (pSMT3-MTB30; pGB9.2-hIL-2) Tice (rBCG30/hIL-2)

Group G: $10^3$ rBCG30/hIL-12 (pSMT3-MTB30; pGB9.2-hIL-12) Tice (rBCG30/hIL-12)

Group H: $10^3$ rBCG(panCD)30 (pNBV1-30) Tice ($10^3$ rBCG(panCD)30)

Group I: $10^6$ rBCG(panCD)30 (pNBV1-30) Tice ($10^6$ rBCG(panCD)30)

Group J: $10^3$ rBCG(panCD)30 (pNBV1-30) Tice—Animals fed diet high in pantothenate ($10^3$ rBCG(panCD)30-diet)

Group K: $10^6$ rBCG(panCD)30 (pNBV1-30) Tice—Animals fed diet high in pantothenate ($10^6$ rBCG(panCD)30-diet)

2. Cutaneous Delayed-type Hypersensitivity (DTH) to Purified Recombinant *M. tuberculosis* 30 kDa Major Secretory Protein (r30)

Five weeks after immunization, 6 guinea pigs in each group were shaved over the back and injected intradermally with 10 μg of purified recombinant *M. tuberculosis* 30 kDa major secretory protein (r30) in 100 μl phosphate buffered saline. After 24 h, the diameter of erythema and induration was measured. A separate group of animals from the one used in the challenge studies—see below—was used for skin-testing to eliminate the possibility that the skin-test itself might influence the outcome. The results are summarized in Table 4.

TABLE 4

Cutaneous DTH - Experiment 3

| Group | Strain | Test Antigen | Erythema (mm ± SE) | Induration (mm ± SE) |
|---|---|---|---|---|
| A | Sham | r30 | 0 ± 0 | 0 ± 0 |
| B | BCG | r30 | 0 ± 0 | 0 ± 0 |
| C | rBCG30 | r30 | 16.5 ± 1.6 | 14.0 ± 3.2 |
| D | rBCG30/hINFγ | r30 | 6.8 ± 1.5 | 1.2 ± 1.2 |
| E | rBCG30/hGM-CSF | r30 | 6.3 ± 1.6 | 3.0 ± 1.9 |
| F | rBCG30/hIL-2 | r30 | 13.5 ± 3.2 | 13.5 ± 3.2 |
| G | rBCG30/hIL-12 | r30 | 5.7 ± 1.9 | 4.3 ± 2.1 |
| H | $10^3$ rBCG(panCD)30 | r30 | 4.3 ± 1.6 | 0 ± 0 |
| I | $10^6$ rBCG(panCD)30 | r30 | 16.1 ± 1.1 | 16.3 ± 1.0 |
| J | $10^3$ rBCG(panCD)30-diet | r30 | 5.8 ± 1.4 | 0 ± 0 |
| K | $10^6$ rBCG(panCD)30-diet | r30 | 15.2 ± 0.8 | 13.0 ± 2.7 |

These results showed that sham-immunized animals (Group A) and animals immunized with the parental BCG Tice strain (Group B) had no erythema or induration upon testing with r30. In contrast, animals immunized with rBCG30 or recombinant BCG strains producing both r30 and a human cytokine, displayed erythema and induration in response to skin-testing. Animals immunized with a high dose of rBCG(panCD)30 requiring pantothenate for growth displayed marked erythema and induration comparable to that of rBCG30. Animals immunized with a low dose of rBCG(panCD)30 requiring pantothenate for growth displayed some erythema but no induration. Interestingly, whether the animals were fed a high or standard amount of pantothenate in their diet did not significantly influence the amount of induration at a given dose of vaccine. Animals immunized with the new strains secreting the 30 kDa major secretory protein in combination with a human immunostimulatory cytokine developed a cell-mediated immune response to r30. In addition, animals immunized with a high vaccine dose of rBCG(panCD)30 developed a cell-mediated immune response to r30.

3. Antibody to Purified Recombinant *M. tuberculosis* 30 kDa Major Protein (r30)

Blood was obtained from the animals described above immediately after they were euthanized, and the serum was assayed for antibody titer to r30 by ELISA, using Costar (Corning, N.Y.) 96-well EIA/RIA High Binding Plates, r30 at 1 μg/well, guinea pig serum diluted 1:64 to 1:1,024,000, alkaline phosphatase-conjugated goat anti-guinea pig IgG (Sigma, St. Louis, Mo.) at a dilution of 1:1,000, and an Alkaline Phosphatase Substrate Kit (BioRad, Hercules, Calif.). Titers of less than 1:64 were scored as 32 for statistical purposes. The results are summarized in Table 5.

TABLE 5

| Antibody to r30 - Experiment 3 | | | |
|---|---|---|---|
| Group | Strain | Test Antigen | Geometric Mean Titer |
| A | Sham | r30 | 84 |
| B | BCG | r30 | 127 |
| C | rBCG30 | r30 | 1154 |
| D | rBCG30/hINFγ | r30 | 48 |
| E | rBCG30/hGM-CSF | r30 | 73 |
| F | rBCG30/hIL-2 | r30 | 49 |
| G | rBCG30/hIL-12 | r30 | 37 |
| H | $10^3$ rBCG(panCD)30 | r30 | 32 |
| I | $10^6$ rBCG(panCD)30 | r30 | 110 |
| J | $10^3$ rBCG(panCD)30-diet | r30 | 37 |
| K | $10^6$ rBCG(panCD)30-diet | r30 | 574 |

These results showed that sham-immunized animals (Group A) and animals immunized with the parental BCG Tice strain (Group B) had relatively low antibody titers to r30. In contrast, animals immunized with rBCG30 had a relatively high titer. Interestingly, animals immunized with recombinant BCG expressing r30 and a cytokine had low titers, indicating that the presence of the cytokine resulted in a diminished antibody response.

Animals immunized with a low dose of rBCG(panCD)30 requiring pantothenate for growth had low titers with or without dietary supplementation with pantothenate. Animals immunized with a high dose of rBCG(panCD)30 requiring pantothenate for growth had a slightly higher antibody titer in the absence of pantothenate dietary supplementation than animals immunized with a low dose of this strain. However, the antibody titer was markedly increased in animals immunized with a high dose of rBCG(panCD)30 requiring pantothenate for growth who were fed a diet rich in pantothenate. The higher titer is consistent with increased survival of the mutant strain in vivo in animals fed pantothenate.

Experiment 4

1. Immunization of Animals

Specific-pathogen free 250-300 g outbred male Hartley strain guinea pigs from Charles River Breeding Laboratories, in groups of 3 or 6, were immunized intradermally with $10^3$ or $10^6$ CFU of one of the following strains:

Group B: $10^3$ BCG Tice Parental Control (BCG) (BCG)

Group C: $10^3$ rBCG30 Tice I (pSMT3-MTB30) (rBCG30)

Group H: $10^3$ rBCG(panCD)30 (pNBV1-30) Tice ($10^3$ rBCG(panCD)30)

Group I: $10^6$ rBCG(panCD)30 (pNBV1-30) Tice ($10^6$ rBCG(panCD)30)

Group J: $10^3$ rBCG(panCD)30 (pNBV1-30) Tice—Animals fed diet high in pantothenate ($10^3$ rBCG(panCD)30-diet)

Group K: $10^6$ rBCG(panCD)30 (pNBV1-30) Tice—Animals fed diet high in pantothenate ($10^6$ rBCG(panCD)30-diet)

2. Lymphocyte Proliferation

Figure 7:
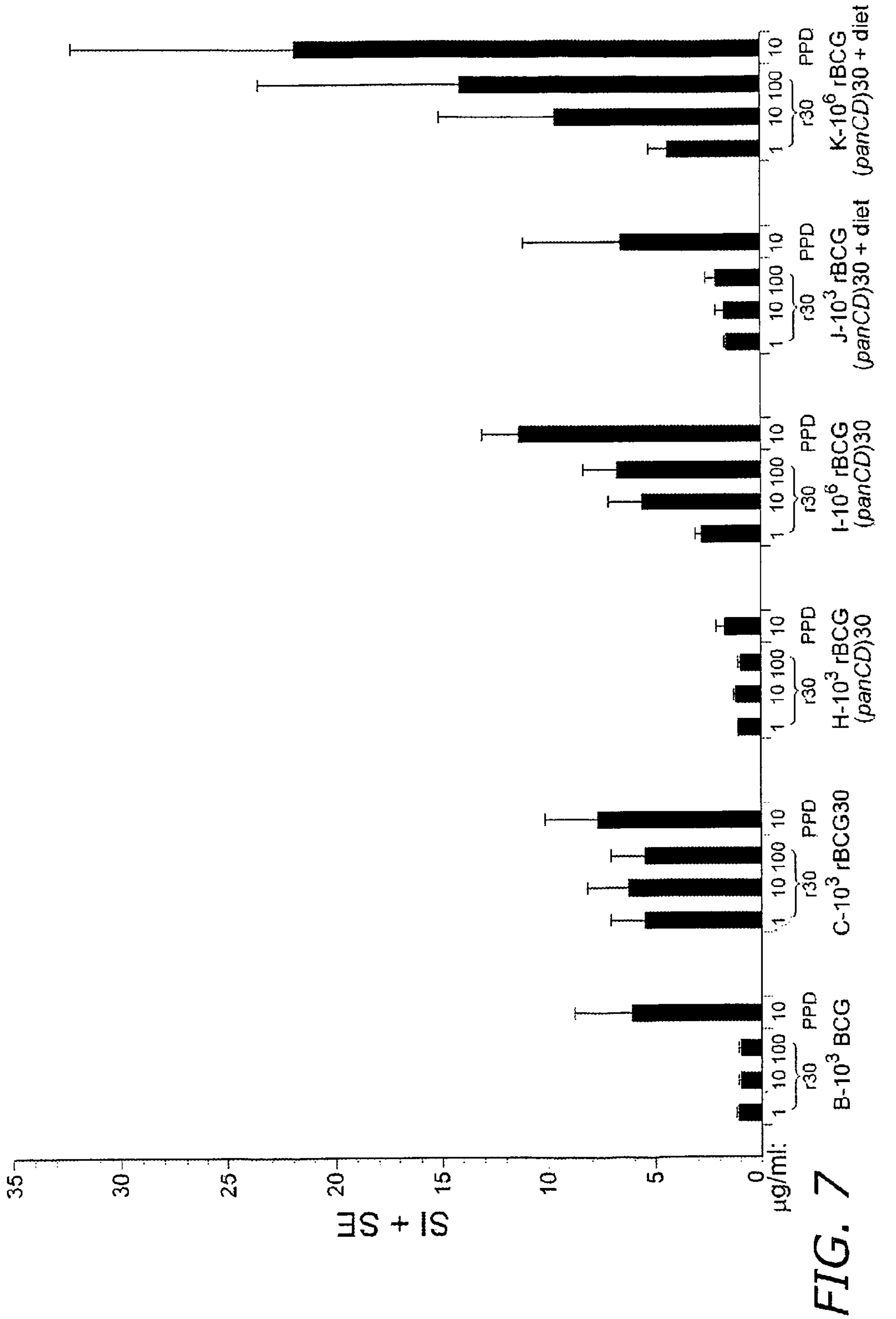
FIG. 7 depicts the proliferation of splenic lymphocytes from guinea pigs immunized with BCG, rBCG30, or various auxotrophic strains of recombinant BCG in response to the *M. tuberculosis* 30 kDa major secretory protein or Purified Protein Derivative (PPD) according to the teachings of the present invention as described in Experiment 4 of Example 4.

Three weeks after immunization, the animals were euthanized and the spleen was removed for lymphocyte proliferation studies. Splenic lymphocytes were purified as described (Pal and Horwitz, Infect. Immun. 60:4781-4792, 1992) and incubated at a final concentration of $10^7$/ml in RPMI1640 containing 12.5 mM HEPES, penicillin (100 U/ml), streptomycin (100 μg/ml), polymyxin B sulfate (100 Units/ml), and 10% fetal calf serum (Gibco) with PPD (10 μg/ml) or with 100, 10, or 1 μg/ml of purified *M. tuberculosis* 30 kDa major secretory protein (r30) in a total volume of 100 μl in microtest wells (96-well round-bottom tissue culture plate; Falcon Labware, Oxnard, Calif.) for 2 days at 37° C. in 5% $CO_2$-95% air and 100% humidity. As negative and positive controls, lymphocytes were incubated with buffer only (RPMI) or with concanavalin A (15 μg/ml). Subsequently, [$^3$H]thymidine incorporation was determined and mean Counts Per Minute (CPM) calculated. Stimulation Indices (SI) were calculated using the following formula: SI=CPM with Antigen/CPM without Antigen. The results are shown in FIG. 7.

Lymphocytes from animals immunized with BCG had a weak proliferative response to r30, but a moderately strong response to PPD. In contrast, lymphocytes from animals immunized with rBCG30 had a strong proliferative response to both r30 and PPD. Lymphocytes from animals immunized with a low dose of rBCG(panCD)30 had a poor proliferative response to both r30 and PPD; however, lymphocytes from animals immunized with a high dose of rBCG(panCD)30 had a strong proliferative response to both r30 and PPD. When animals immunized with a low dose of rBCG(panCD)30 were fed a high pantothenate diet, lymphocytes from these animals had an increased proliferative response. Similarly, when animals immunized with a high dose of rBCG(panCD)30 were fed a high pantothenate diet, lymphocytes from these animals showed an increased proliferative response.

Experiment 5

1. Immunization of Animals

Specific-pathogen free 250-300 g outbred male Hartley strain guinea pigs from Charles River Breeding Laboratories, in groups of 3 were immunized intradermally with $10^6$-$10^7$ CFU of one of the following strains:

Group A: BCG Tice Parental Control (BCG)

Group B: rBCG30 Tice I (pSMT3-MTB30) (rBCG30)

Group C: rBCG(trpD) Tice (rBCG(trpD))

Group D: rBCG(trpD)30 (pSMT3-MTB30) Tice (rBCG(trpD)30)

Group E: rBCG(trpD) Tice—Animals fed diet high in tryptophan (rBCG(trpD)-diet)

Group F: rBCG(trpD)30 (pSMT3-MTB30) Tice—Animals fed diet high in tryptophan (rBCG(trpD)30-diet)

Group G: rBCG(panCD) Tice (rBCG(panCD))

Group H: rBCG(panCD) Tice—Animals fed diet high in pantothenate (rBCG(panCD)-diet)

Group I: rBCG(mbtB) Tice—Grown in medium containing a low mycobactin J concentration (rBCG(mbtB) Lo Fe)

Group J: rBCG(mbtB) Tice—Grown in medium containing a high mycobactin J concentration (rBCG(mbtB) Hi Fe)

2. Lymphocyte Proliferation

Figure 8:
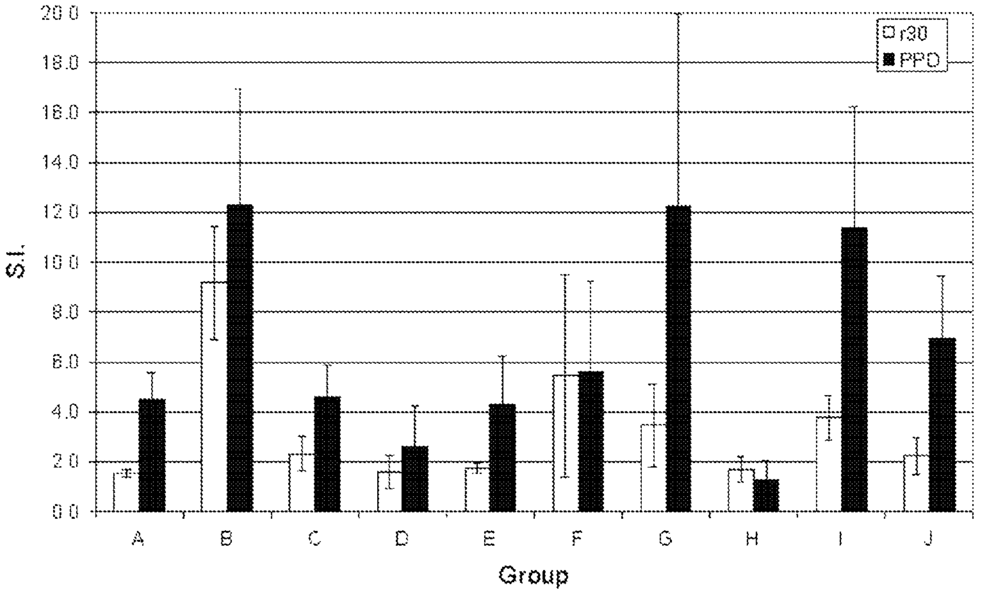
FIG. 8 depicts proliferation of splenic lymphocytes of guinea pigs immunized with BCG, rBCG30, or various auxotrophic or growth-restricted strains of recombinant BCG in response to the *M. tuberculosis* 30 kDa major secretory protein or PPD according to the teachings of the present invention as described in Experiment 5 of Example 4.

Three weeks after immunization, the animals were euthanized and the spleen was removed for lymphocyte proliferation studies. Splenic lymphocytes were purified and incubated at a final concentration of $10^7$/ml in RPMI1640 containing 12.5 mM HEPES, penicillin (100 U/ml), streptomycin (100 μg/ml), polymyxin B sulfate (100 Units/ml), and 10% fetal calf serum with PPD (10 μg/ml) or with 100 μg/ml of purified *M. tuberculosis* 30 kDa major secretory protein (r30) in a total volume of 100 μl in microtest wells for 2 days at 37° C. in 5% $CO_2$-95% air and 100% humidity. As negative and positive controls, lymphocytes were incubated with buffer only (RPMI) or with concanavalin A (15 μg/ml). Subsequently, [$^3$H]thymidine incorporation was determined and mean CPM calculated. Stimulation Indices (SI) were calculated using the following formula: SI=CPM with Antigen/CPM without Antigen. The results are shown in FIG. 8.

Lymphocytes from animals immunized with BCG had a weak proliferative response to r30, but a moderately strong response to PPD. In contrast, lymphocytes from animals immunized with rBCG30 had a strong proliferative response to both r30 and PPD. Lymphocytes from animals immunized with rBCG(trpD) or rBCG(trpD)30 responded similarly to BCG. When animals immunized with rBCG(trpD) were fed a high tryptophan diet, lymphocytes from these animals showed a response similar to lymphocytes from animals immunized with rBCG(trpD) and not fed a high tryptophan diet. However, when animals immunized with rBCG(trpD)30 were fed a high tryptophan diet, lymphocytes from these animals showed an increased proliferative response compared with lymphocytes from animals immunized with rBCG (trpD)30 and not fed a high tryptophan diet. Lymphocytes from animals immunized with rBCG(panCD) showed a modest response to r30 and a moderately strong response to PPD. When animals immunized with rBCG(panCD) were fed a high pantothenate diet, lymphocyte proliferative responses to r30 and PPD did not increase but instead somewhat decreased. Lymphocytes from animals immunized with rBCG(mbtB) grown in the presence of low mycobactin J proliferated moderately strongly to both r30 and PPD. Similar lymphocyte proliferative responses were seen in lymphocytes from animals immunized with rBCG(mbtB) grown in the presence of a high level of mycobactin J.

Experiment 6

1. Immunization of Animals

Specific-pathogen free 250-300 g outbred male Hartley strain guinea pigs from Charles River Breeding Laboratories, in groups of 15 or 21, were sham-immunized by intradermal administration of buffer (15 animals total) or immunized intradermally with $10^3$ or $10^6$ CFU of one of the following strains (21 animals/group):

Group A: Sham-immunized (Sham)

Group B: $10^3$ BCG Tice Parental Control (BCG)

Group C: $10^3$ rBCG30 Tice I (pSMT3-MTB30) (rBCG30)

Group D: $10^3$ rBCG30/hINFγ (pSMT3-MTB30; pGB9.2-hINFγ) Tice (rBCG30/hINFγ)

Group E: $10^3$ rBCG/hINFγ (pGB9.2-hINFγ) Tice (rBCG/hINFγ)

Group F: $10^3$ BCG Tice Parental Control—Grown in medium containing 0.01% Tyloxapol ($10^3$ BCG-Tyl)

Group G: $10^3$ rBCG(mbtB) Tice—Grown in medium containing a high mycobactin J concentration and 0.01% Tyloxapol ($10^3$ rBCG(mbtB) Hi Fe)

Group H: $10^3$ rBCG(mbtB)30 II (pNBV1-30) Tice—Grown in medium containing a high mycobactin J concentration and 0.01% Tyloxapol ($10^3$ rBCG(mbtB)30 Hi Fe)

Group I: $10^6$ BCG Tice Parental Control—Grown in medium containing 0.01% Tyloxapol ($10^6$ BCG-Tyl)

Group J: $10^6$ rBCG(mbtB) Tice—Grown in medium containing a high mycobactin J concentration and 0.01% Tyloxapol ($10^6$ rBCG(mbtB) Hi Fe)

Group K: $10^6$ rBCG(mbtB)30 II (pNBV1-30) Tice—Grown in medium containing a high mycobactin J concentration and 0.01% Tyloxapol ($10^6$ rBCG(mbtB)30 Hi Fe)

2. Cutaneous Delayed-type Hypersensitivity (DTH) to Purified Recombinant *M. tuberculosis* 30 kDa Major Secretory Protein (r30)

Ten weeks after immunization, 6 guinea pigs in each group were shaved over the back and injected intradermally with 10 μg of purified recombinant *M. tuberculosis* 30 kDa major secretory protein (r30) in 100 μl phosphate buffered saline. After 24 h, the diameter of erythema and induration was measured. A separate group of animals from the one used in the challenge studies—see below—was used for skin-testing to eliminate the possibility that the skin-test itself might influence the outcome. The results are summarized in Table 6.

TABLE 6

Cutaneous DTH - Experiment 6

| Group | Strain | Test Antigen | Erythema (mm ± SE) | Induration (mm ± SE) |
|---|---|---|---|---|
| A | Sham | r30 | 2.1 ± 1.0 | 0 ± 0 |
| B | BCG | r30 | 5.0 ± 1.3 | 0 ± 0 |
| C | rBCG30 | r30 | 17.8 ± 2.1 | 16.5 ± 3.4 |
| D | rBCG30/hINFγ | r30 | 4.3 ± 1.6 | 0 ± 0 |
| E | rBCG/hINFγ | r30 | 6.6 ± 2.5 | 0 ± 0 |
| F | $10^3$ BCG-Tyl | r30 | 7.3 ± 1.6 | 1.7 ± 1.7 |
| G | $10^3$rBCG(mbtB) Hi Fe | r30 | 1.5 ± 1.0 | 0 ± 0 |
| H | $10^3$rBCG(mbtB)30 Hi Fe | r30 | 8.8 ± 2.2 | 0 ± 0 |
| I | $10^6$BCG-Tyl | r30 | 4.0 ± 2.2 | 0 ± 0 |
| J | $10^6$rBCG(mbtB) Hi Fe | r30 | 0 ± 0 | 0 ± 0 |
| K | $10^6$rBCG(mbtB)30 Hi Fe | r30 | 15.0 ± 0.8 | 10.3 ± 3.3 |

These results showed that sham-immunized animals (Group A) and animals immunized with the parental BCG Tice strain (Groups B, F, and I) had little or no induration upon testing with r30 whether the strain was grown in medium containing tyloxapol or not and whether or not a high dose was administered. Similarly, animals immunized with a growth-limited vaccine [rBCG(mbtB)] not over-expressing the 30 kDa protein had no induration upon testing with r30, whether a low dose (Group G) or high dose (Group J) of the vaccine was administered. In contrast, animals immunized with a recombinant BCG strain over-expressing r30 (Group C) had induration in response to r30. Similarly, animals immunized with the growth-limited strain rBCG(mbtB)30, when administered as a high dose (Group K) showed induration upon testing with r30. Animals immunized with a low dose of the growth-limited strain rBCG(mbtB)30 (Group H) showed no induration upon testing with r30. Interestingly, as previously observed, the recombinant BCG expressing both r30 and human interferon gamma (Group D) did not show induration upon testing with r30, although it did display some erythema.

3. Protective Immunity to Aerosol Challenge

Ten weeks after immunization, the remaining animals in Groups A-K were challenged with an aerosol generated from a 10 ml single-cell suspension containing $7.5\times10^4$ CFU of *M. tuberculosis*. This aerosol dose delivered ~10 live bacilli to the lungs of each animal. The airborne route of infection was used because this is the natural route of infection for pulmonary tuberculosis. A relatively large dose was used so as to induce measurable clinical illness in 100% of control animals within a relatively short time frame (10 weeks). Afterwards, guinea pigs were individually housed in stainless steel cages contained within a laminar flow biohazard safety enclosure and allowed free access to standard laboratory chow and water. The animals were observed for illness and weighed weekly for 10 weeks and then euthanized. The right lung and spleen of each animal was removed and cultured for CFU of *M. tuberculosis* on Middlebrook 7H11 agar for two weeks at 37° C., 5% $CO_2$-95% air atmosphere. The results of the assay for CFU in the lungs and spleens are shown in Table 7.

TABLE 7

CFU in Lungs and Spleens - Experiment 6

| Group | Strain | Lung (Mean Log CFU ± SE) | Spleen (Mean Log CFU ± SE) |
|---|---|---|---|
| A | Sham | 6.63 ± 0.22 | 6.41 ± 0.22 |
| B | BCG | 5.17 ± 0.09 | 4.48 ± 0.06 |
| C | rBCG30 | 4.23 ± 0.13 | 3.47 ± 0.09 |
| D | rBCG30/hINFγ | 4.03 ± 0.09 | 2.57 ± 0.26 |
| E | rBCG/hINFγ | 5.11 ± 0.07 | 4.39 ± 0.05 |
| F | $10^3$ BCG-Tyl | 4.96 ± 0.08 | 4.59 ± 0.07 |
| G | $10^3$rBCG(mbtB) Hi Fe | 5.37 ± 0.16 | 4.79 ± 0.18 |
| H | $10^3$rBCG(mbtB)30 Hi Fe | 5.01 ± 0.16 | 4.63 ± 0.26 |
| I | $10^6$BCG-Tyl | 5.17 ± 0.09 | 4.31 ± 0.08 |
| J | $10^6$rBCG(mbtB) Hi Fe | 4.83 ± 0.12 | 4.23 ± 0.12 |
| K | $10^6$rBCG(mbtB)30 Hi Fe | 4.56 ± 0.21 | 3.94 ± 0.21 |

These results showed that animals immunized with BCG or any recombinant BCG strain had much lower CFU in the lungs and spleens than the sham immunized animals.

Animals immunized with the recombinant BCG strain secreting both the *M. tuberculosis* 30 kDa major secretory protein and human interferon gamma (rBCG30/hINFγ) had markedly fewer CFU in the lung and spleen than animals immunized with rBCG30; animals immunized with rBCG30/hINFγ had 0.2 logs fewer CFU in the lung and 0.9 logs fewer CFU in the spleen than rBCG30-immunized animals.

Importantly, animals immunized with the recombinant BCG vaccine secreting only human interferon gamma did not show protection significantly different from BCG. Hence, it was the co-expression of both the 30 kDa protein and human interferon gamma that was necessary for the superior efficacy of the rBCG30/hINFγ vaccine.

Remarkably, animals immunized with the high dose of the growth-limited recombinant BCG strain over-expressing the *M. tuberculosis* 30 kDa major secretory protein [rBCG (mbtB)30]) showed an impressive reduction in CFU in animal organs compared with BCG, whether or not the BCG vaccine was grown in tyloxapol. There was no significant difference in potency of BCG vaccines grown in the presence or the absence of tyloxapol.

Experiment 7

1. Immunization of Animals

Specific-pathogen free 250-300 g outbred male Hartley strain guinea pigs from Charles River Breeding Laboratories, in groups of 15 or 21, were sham-immunized by intradermal administration of buffer (15 animals total) or immunized intradermally with $10^3$ or $10^6$ CFU of one of the following strains (21 animals/group):

Group A: Sham-immunized (Sham)

Group B: $10^3$ BCG Tice Parental Control ($10^3$ BCG)

Group C: $10^3$ rBCG30 Tice I (pSMT3-MTB30) (rBCG30)

Group D: $10^6$ BCG Tice Parental Control ($10^6$ BCG)

Group E: $10^6$ rBCG(mbtB)30 II (pNBV1-30) Tice—Grown in medium containing a high mycobactin J concentration and 0.01% Tyloxapol ($10^6$ rBCG(mbtB)30 Hi Fe)

Group F: $10^3$ rBCG(panCD)30 Tice($10^3$ rBCG(panCD) 30)

Group G: $10^6$ rBCG(panCD)30 Tice ($10^6$ rBCG(panCD) 30)

Group H: $10^3$ rBCG(panCD)30 Tice—Animals fed diet high in pantothenate ($10^3$ rBCG(panCD)30+Diet)

Group I: $10^6$ rBCG(panCD)30 Tice—Animals fed diet high in pantothenate ($10^6$ rBCG(panCD)30+Diet)

Group J: $10^6$ rBCG(trpD)30 (pSMT3-MTB30) Tice ($10^6$ rBCG(trpD)30)

Group K: $10^8$ rBCG(panCD)30 Tice ($10^8$ rBCG(panCD) 30)

2. Cutaneous Delayed-type Hypersensitivity (DTH) to Purified Recombinant *M. tuberculosis* 30 kDa Major Secretory Protein (r30)

Ten weeks after immunization, 6 guinea pigs in each group were shaved over the back and injected intradermally with 10 μg of purified recombinant *M. tuberculosis* 30 kDa major secretory protein (r30) in 100 μl phosphate buffered saline. After 24 h, the diameter of erythema and induration was measured. A separate group of animals from the one used in the challenge studies—see below—was used for skin-testing to eliminate the possibility that the skin-test itself might influence the outcome. The results are summarized in Table 8.

TABLE 8

Cutaneous DTH - Experiment 7

| Group | Strain | Test Antigen | Erythema (mm ± SE) | Induration (mm ± SE) |
|---|---|---|---|---|
| A | Sham | r30 | 1.5 ± 1.0 | 0 ± 0 |
| B | $10^3$ BCG | r30 | 8.5 ± 1.8 | 0 ± 0 |
| C | rBCG30 | r30 | 10.7 ± 2.3 | 2.5 ± 2.5 |
| D | $10^6$ BCG | r30 | 11.0 ± 0.8 | 0 ± 0 |
| E | $10^6$ rBCG(mbtB)30 Hi Fe | r30 | 14.0 ± 0.9 | 10.0 ± 3.2 |
| F | $10^3$ rBCG(panCD)30 | r30 | 2.5 ± 1.7 | 0 ± 0 |
| G | $10^6$ rBCG(panCD)30 | r30 | 12.8 ± 0.8 | 2.3 ± 2.3 |
| H | $10^3$ rBCG(panCD)30 + Diet | r30 | 1.3 ± 1.3 | 0 ± 0 |
| I | $10^6$ rBCG(panCD)30 + Diet | r30 | 11.0 ± 1.6 | 5.0 ± 3.2 |
| J | $10^6$ rBCG(trpD)30 | r30 | 12.0 ± 2.7 | 5.8 ± 3.7 |
| K | $10^8$ rBCG(panCD)30 | r30 | 11.7 ± 1.0 | 6.3 ± 2.9 |

These results showed that sham-immunized animals (Group A) and animals immunized with the parental BCG Tice strain (Groups B and D) had no induration upon testing with r30 whether the dose was high or low. Similarly, animals immunized with a low dose of rBCG(panCD)30 with or without a dietary supplement had no induration upon testing with r30. In contrast, animals immunized with rBCG30 as well as with high doses ($10^6$ or $10^8$) of rBCG(mbtB)30 Hi Fe, rBCG (panCD)30, and rBCG(trpD)30 had relatively high amounts of induration in response to r30.

3. Protective Immunity to Aerosol Challenge

Ten weeks after immunization, the remaining animals in Groups A-K were challenged with an aerosol generated from a 10 ml single-cell suspension containing $7.5\times10^4$ CFU of *M. tuberculosis*. This aerosol dose delivered ~10 live bacilli to the lungs of each animal. Afterwards, guinea pigs were individually housed in stainless steel cages contained within a laminar flow biohazard safety enclosure and allowed free access to standard laboratory chow and water. The animals were observed for illness and weighed weekly for 10 weeks and then euthanized. The right lung and spleen of each animal was removed and cultured for CFU of *M. tuberculosis* on Middlebrook 7H11 agar for two weeks at 37° C., 5% $CO_2$-95% air atmosphere. The results of the assay for CFU in the lungs and spleens are shown in Table 9.

TABLE 9

CFU in Lungs and Spleens - Experiment 7

| Group | Strain | Lung (Mean Log CFU ± SE) | Spleen (Mean Log CFU ± SE) |
|---|---|---|---|
| A | Sham | 6.73 ± 0.16 | 6.74 ± 0.15 |
| B | $10^3$ BCG | 4.22 ± 0.08 | 3.95 ± 0.08 |
| C | rBCG30 | 3.48 ± 0.11 | 2.34 ± 0.14 |
| D | $10^6$ BCG | 4.09 ± 0.07 | 3.80 ± 0.07 |
| E | $10^6$ rBCG(mbtB)30 Hi Fe | 4.24 ± 0.05 | 3.78 ± 0.05 |
| F | $10^3$ rBCG(panCD)30 | 5.40 ± 0.06 | 5.28 ± 0.06 |
| G | $10^6$ rBCG(panCD)30 | 4.72 ± 0.10 | 4.77 ± 0.13 |
| H | $10^3$ rBCG(panCD)30 + Diet | 5.07 ± 0.08 | 4.94 ± 0.11 |
| I | $10^6$ rBCG(panCD)30 + Diet | 4.57 ± 0.10 | 4.46 ± 0.09 |
| J | $10^6$ rBCG(trpD)30 | 4.83 ± 0.09 | 4.67 ± 0.11 |
| K | $10^8$ rBCG(panCD)30 | 4.27 ± 0.07 | 4.01 ± 0.10 |

These results showed that animals immunized with BCG or any recombinant BCG strain had much lower CFU in the lungs and spleens than the sham immunized animals.

Animals immunized with the growth-restricted strain rBCG(mbtB)30 Hi Fe had CFU comparable to BCG-immunized animals in their organs.

Animals immunized with $10^3$, $10^6$, and $10^8$ rBCG(panCD) 30 showed a dose-dependent effect on CFU in their organs; the higher the dose the lower the CFU counts. The effect on dose was statistically significant in both the lung and spleen ($P<0.0001$ by ANOVA).

Animals immunized with rBCG(panCD)30 and fed a diet rich in pantothenate had fewer CFU than animals immunized with the same dose of rBCG(panCD)30 and not fed a diet rich in pantothenate. The effect on diet was statistically significant ($P=0.008$ in the lung and $P=0.003$ in the spleen by ANOVA).

Example 5

Clearance of Vaccines in Guinea Pigs

Specific-pathogen free 250-300 g outbred male Hartley strain guinea pigs from Charles River Breeding Laboratories, in groups of 24, were immunized intradermally with $10^6$ CFU of one of the following strains:

Group A: $10^6$ BCG Tice Parental Control (BCG)

Group B: $10^6$ rBCG(mbtB)30 II (pNBV1-30) Tice—Grown in medium containing a high mycobactin J concentration (rBCG(mbtB)30)

Group C: $10^6$ rBCG(panCD)30 Tice (rBCG(panCD)30)

Figure 9:
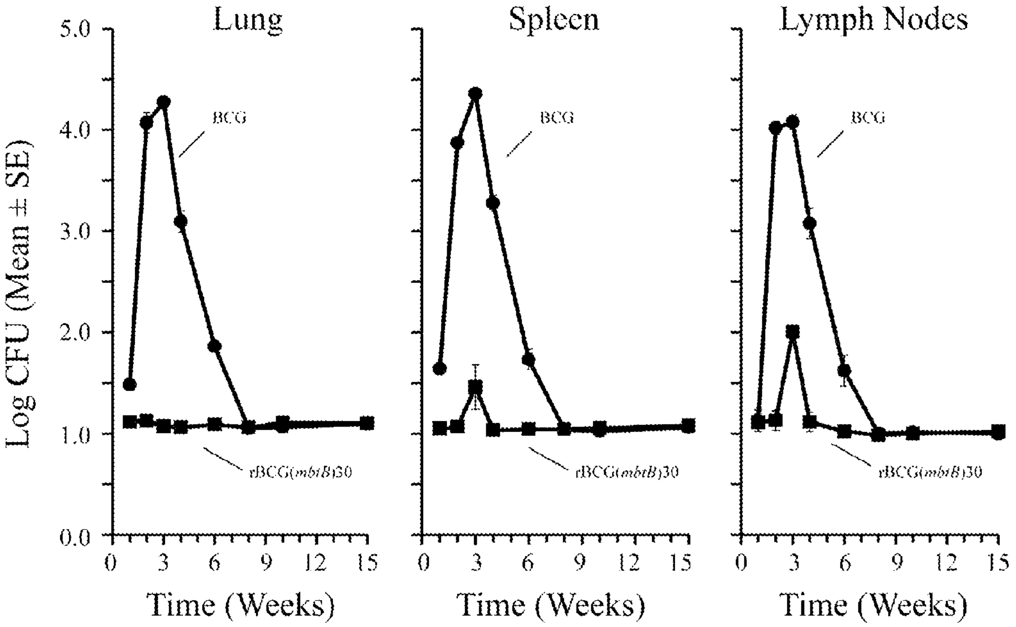
FIG. 9 depicts replication of rBCG(mbtB)30 in guinea pigs according to the teachings of the present invention.
Figure 10:
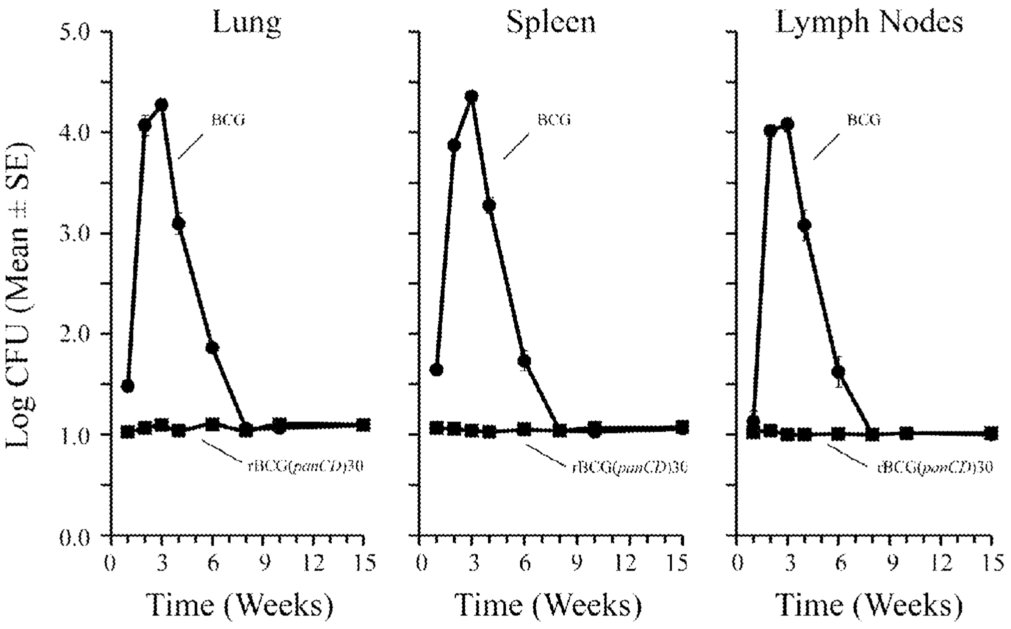
FIG. 10 depicts replication of rBCG(panCD)30 in guinea pigs according to the teachings of the present invention.

At 1, 2, 3, 4, 6, 8, 10, and 15 weeks after immunization, three animals per group were euthanized and CFU of BCG, rBCG(mbtB)30, and rBCG(panCD)30 in the lung, spleen, and lymph nodes were assayed (FIGS. 9 and 10; the results for BCG-immunized animals are repeated in each figure). Data are presented as the mean Log CFU±SE. The limit of detection was 1 Log CFU.

These results showed that the persistence of the growth-restricted rBCG(mbtB)30 strain was much less than the persistence of BCG in guinea pig organs (FIG. 9).

The rBCG(panCD)30 strain also showed much less persistence than BCG in guinea pig organs (FIG. 10).

Example 6

Virulence of Vaccines in SCID Mice

Fox Chase SCID mice (CB-17/lcr-Prkdc$^{scid}$/Crl) from Charles River Breeding Laboratories in groups of 20 were challenged by intravenous tail vein injection with $10^6$ CFU or $10^8$ CFU of one of the following strains or injected with buffer (PBS):

Group A: Sham-challenged with PBS buffer (Sham)

Group B: $10^6$ BCG Tice Parental Control ($10^6$ BCG)

Group C: $10^6$ rBCG(mbtB)30 II (pNBV1-30) Tice—Grown in medium containing a high mycobactin concentration ($10^6$ rBCG(mbtB)30)

Group D: $10^6$ rBCG(panCD)30 Tice ($10^6$ rBCG(panCD) 30)

Group E: $10^8$ rBCG(mbtB)30 II (pNBV1-30) Tice—Grown in medium containing a high mycobactin concentration ($10^8$ rBCG(mbtB)30)

Group F: $10^8$ rBCG(panCD)30 Tice ($10^8$ rBCG(panCD) 30)

Group G: $10^8$ BCG Tice Parental Control ($10^8$ BCG)

Figure 11:
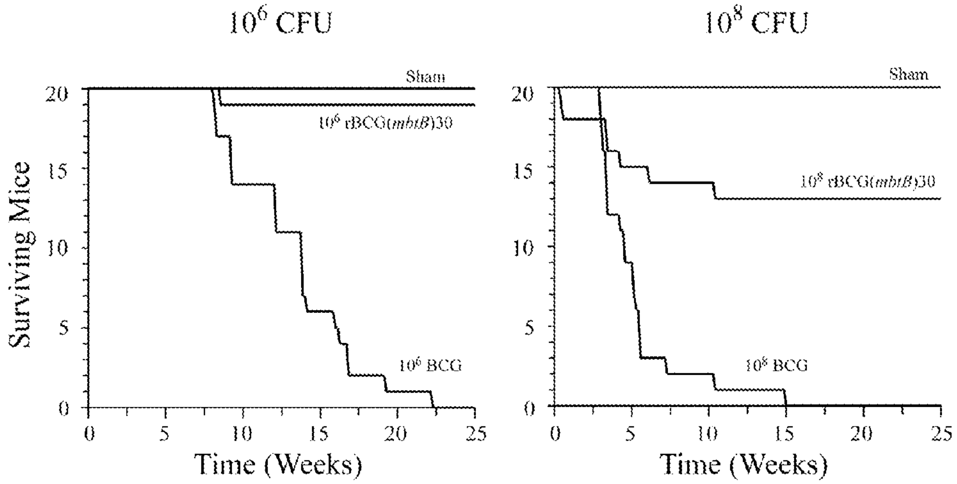
FIG. 11 depicts the survival of SCID mice infected with rBCG(mbtB)30 according to the teachings of the present invention.
Figure 12:
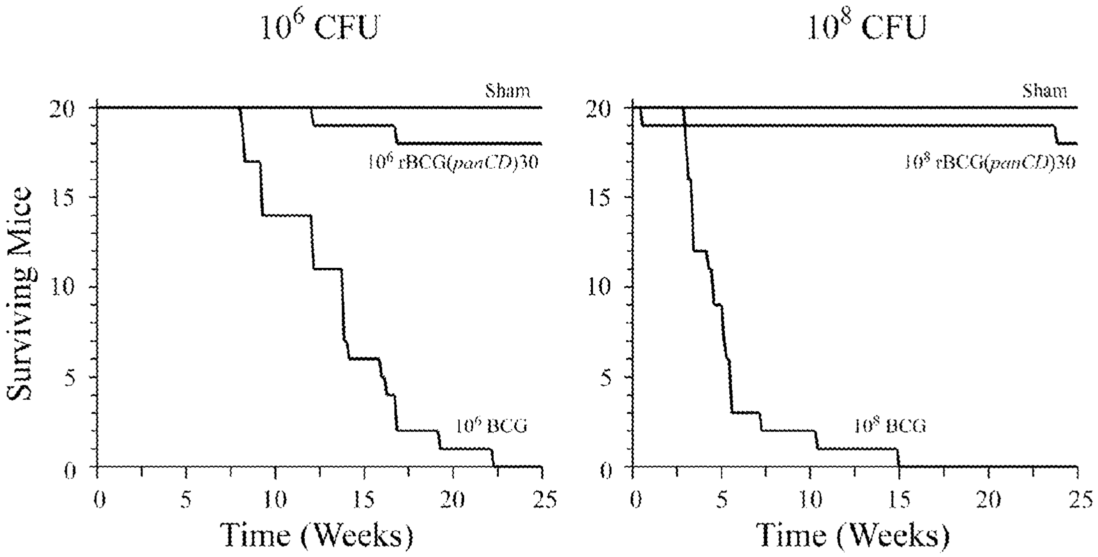
FIG. 12 depicts the survival of SCID mice infected with rBCG(panCD)30 according to the teachings of the present invention.

Survival was monitored for 25 weeks (FIGS. 11 and 12; the results for sham and BCG-immunized animals are repeated in each figure).

These results showed that the growth-restricted rBCG (mbtB)30 strain was much safer than BCG in the immunocompromised SCID mouse (FIG. 11). Ata dose of $10^6$ CFU, the vaccine was essentially avirulent, whereas BCG at this dose killed all animals by 22 weeks. At an extremely high dose of $10^8$ CFU, the vaccine was somewhat more virulent than sham immunization, but still much less virulent than BCG, which killed all animals by 15 weeks.

The rBCG(panCD)30 strain was also much safer than BCG, and was essentially avirulent at challenge doses of both $10^6$ CFU and $10^8$ CFU (FIG. 12).

Example 7 rBCGs Expressing Proteins Integrated into Genomic DNA

In another embodiment of the present invention, the genes encoding immunogenic intracellular pathogen proteins and/or cytokines can be integrated into the chromosome. For example, rBCG strains have been generated that over-express the *M. tuberculosis* 30 kDa protein from the chromosome through an allelic exchange procedure. A cassette containing the fbpB gene (encoding the 30 kDa protein) with expression driven from the rrs promoter was cloned into a wild-type glnA1 locus, just downstream of glnA1. This glnA1 locus with the fbpB insertion was cloned into phEX2 (a derivative of phEX1, itself a derivative of phAE87 [Bardarov et al., Microbiol. 148:3007-3017, 2002]) and specialized transducing phage was prepared by electroporating the plasmid into *M. smegmatis*. The phage was used to infect BCG strains and clones over-expressing the 30 kDa protein were selected.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An immunogenic composition comprising:

a growth regulatable recombinant Bacille Calmette Guérin (rBCG) expressing at least one *Mycobacteria* major extracellular protein selected from the group consisting of 12 kDa protein, 14 kDa protein, 16 kDa protein, 23.5 kDa protein, 24 kDa protein, 30 kDa protein, 32A kDa protein, 32B kDa protein, 45 kDa protein, 58 kDa protein, 71 kDa protein, 80 kDa protein, and 110 KD protein, and combinations thereof, wherein at least one of said at least one *Mycobacteria* major extracellular proteins are expressed on one or more extrachromosomal nucleic acid sequences, wherein said growth regulatable rBCG is selected from the group consisting of an auxotroph wherein pantothenic acid is used to regulate the growth of said auxotroph, and a siderophore mutant wherein the siderophore is mycobactin or exochelin, and wherein said *Mycobacteria* major extracellular proteins are over-expressed and secreted.

2. The immunogenic composition according to claim 1 wherein each of said at least one *Mycobacteria* major extracellular proteins are expressed from different extrachromosomal nucleic acid sequences.

3. An immunogenic composition comprising:

a growth regulatable recombinant rBCG expressing at least one *Mycobacteria* major extracellular protein selected from the group consisting of 12 kDa protein, 14 kDa protein, 16 kDa protein, 23.5 kDa protein, 24 kDa protein, 30 kDa protein, 32A kDa protein, 32B kDa protein, 45 kDa protein, 58 kDa protein, 71 kDa protein, 80 kDa protein, and 110 KD protein, and combinations thereof, and wherein at least one of said at least one *Mycobacteria* major extracellular proteins are integrated into the rBCG genome under the control of a strong promoter and over-expressed, and wherein said growth regulatable rBCG is selected from the group consisting of an auxotroph wherein pantothenic acid is used to regulate the growth of said auxotroph, and a siderophore mutant wherein the siderophore is mycobactin or exochelin.

4. The immunogenic composition according to claim 3 wherein more than one of said at least one *Mycobacteria* major extracellular proteins are integrated into the rBCG genome under the control of a strong promoter and over-expressed.

5. The immunogenic composition according to claim 1 wherein said major extracellular proteins are non-fusion proteins.

6. The immunogenic composition according to claim 1 wherein said *Mycobacteria* major extracellular protein is from a *Mycobacteria* species selected from the group consisting of *Mycobacterium tuberculosis, Mycobacterium bovis, Mycobacterium leprae*, and *Mycobacterium avium* intracellulare.

7. The immunogenic composition according to claim 1 wherein said *Mycobacteria* major extracellular protein is the 30 kDa protein.

8. The immunogenic composition according to claim 1 further comprising a gene capable of expressing at least one cytokine selected from the group consisting of interferon gamma, interleukin-2, interleukin-12, interleukin-4 receptor, granulocyte macrophage colony stimulating factor, and combinations thereof.

9. An immunogenic composition comprising a growth regulatable recombinant attenuated intracellular pathogen wherein said growth regulatable recombinant attenuated intracellular pathogen expresses at least one major extracellular protein of an intracellular pathogen under the control of a strong promoter such that the major extracellular protein is over-expressed, and wherein said growth regulatable recombinant attenuated intracellular pathogen is an rBCG selected from the group consisting of an auxotroph wherein pantothenic acid is used to regulate the growth of said auxotroph, and a siderophore mutant wherein the siderophore is mycobactin or exochelin.

10. The immunogenic composition of claim 9 wherein said growth regulatable recombinant attenuated intracellular pathogen is of the same species as the intracellular pathogen against which the immunogenic composition is directed.

11. The immunogenic composition of claim 9 wherein said growth regulatable recombinant attenuated intracellular pathogen is of a different species than the intracellular pathogen against which the immunogenic composition is directed.

12. The immunogenic composition of claim 9 wherein said at least one major extracellular protein is from an intracellular pathogen selected from the group consisting of *Mycobacterium bovis, M. tuberculosis, M. leprae, M. kansasii, M. avium, Mycobacterium* sp., *Legionella pneumophila, L. longbeachae, L. bozemanii, Legionella* sp., *Rickettsia rickettsii, Rickettsia typhi, Rickettsia* sp., *Ehrlichia chaffeensis, Ehrlichia phagocytophila* geno group, *Ehrlichia* sp., *Coxiella burnetii, Leishmania* sp., Toxpolasma *Trypanosoma cruzi, Chlamydia pneumoniae, Chlamydia* s.p, *Listeria monocytogenes, Listeria* sp., *Histoplasma* sp., *Francisella tularensis, Brucella* species, *Yersinia pestis, Bacillus anthracis*, and *Salmonella typhi.*

13. An immunogenic composition comprising a growth regulatable siderophore-dependent rBCG wherein said growth regulatable rBCG expresses the kDa *Mycobacteria* major extracellular protein and interferon gamma, wherein a nucleic acid sequence encoding for said 30 kDa *Mycobacteria* major extracellular protein is incorporated into the intracellular pathogen's chromosome(s) under a strong promoter such that said 30 kDa *Mycobacteria* major extracellular protein is over-expressed and wherein mycobactin is used to allow growth of the rBCG in vitro.

14. The immunogenic composition according to claim 3 wherein said major extracellular proteins are non-fusion proteins.

15. The immunogenic composition according to claim 3 wherein said *Mycobacteria* major extracellular protein is from a *Mycobacteria* species selected from the group consisting of *Mycobacterium tuberculosis, Mycobacterium bovis, Mycobacterium leprae*, and *Mycobacterium avium* intracellulare.

16. The immunogenic composition according to claim 3 wherein said *Mycobacteria* major extracellular protein is the 30 kDa protein.

17. The immunogenic composition according to claim 3 further comprising a gene capable of expressing at least one cytokine selected from the group consisting of interferon gamma, interleukin-2, interleukin-12, interleukin-4 receptor, granulocyte macrophage colony stimulating factor, and combinations thereof.

* * * * *